(12) United States Patent
Borer et al.

(10) Patent No.: US 6,472,534 B2
(45) Date of Patent: Oct. 29, 2002

(54) METHODS FOR THE PREPARATION OF INTERMEDIATES IN THE SYNTHESIS OF HIV-PROTEASE INHIBITORS

(75) Inventors: Bennett C. Borer, La Jolla; Scott E. Zook; Juliette K. Busse, both of San Diego, all of CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 09/986,146

(22) Filed: Nov. 7, 2001

(65) Prior Publication Data

US 2002/0038033 A1 Mar. 28, 2002

Related U.S. Application Data

(62) Division of application No. 09/690,093, filed on Oct. 17, 2000.
(60) Provisional application No. 60/160,695, filed on Oct. 21, 1999.

(51) Int. Cl.$^7$ ..................... C07D 263/08; C07D 263/12
(52) U.S. Cl. ....................................... 548/237; 548/239
(58) Field of Search .................................. 548/237, 239

(56) References Cited

U.S. PATENT DOCUMENTS

| 5,484,926 A | 1/1996 | Dressman et al. .......... 546/114 |
| 5,527,829 A | 6/1996 | Kalish et al. ............... 514/604 |
| 5,863,950 A | 1/1999 | Reich et al. ................ 514/616 |
| 5,925,759 A | * 7/1999 | Babu |
| 6,001,851 A | 12/1999 | Albizati et al. ............. 514/307 |

FOREIGN PATENT DOCUMENTS

| AU | 717637 | 4/1997 |
| WO | WO 94/19351 | 9/1994 |
| WO | WO 97/11937 | 4/1997 |
| WO | WO 97/11938 | 4/1997 |

OTHER PUBLICATIONS

C. Flexner, "HIV–Protease Inhibitors", New England Journal of Medicine (1998) vol. 338 No. (18), pp. 1281–1292.
T. Inaba et al., "A Practical Synthesis of Nelfinavir, an HIV–Protease Inhibitor, Using a Novel Chiral C4 Building Block: (5R,6S)–2,2–Dimethyl–5–hydroxy–1,3–dioxepan–6–ylammonium Acetate", J. Org. Chem. (1998) vol. 63, No. 22, pp. 7582–7583.
K. J. Wilson, et al., "A Remarkable Base–Induced Rearrangement of Hydroxy Oxazolines to Amido Tetrahydrofurans", J. Org. Chem. (1993) vol. 58, No. 23, pp. 6180–6181.
H. Yamazaki et al., "Syntheses and Antiulcer Activities of 2–Aminonorbornene Derivatives", Chem. Pharm. Bull. (1992) vol. 40, No. 1, pp. 102–108.
S. E. Schaus et al., "Practical Synthesis of Enantiopure Cyclic 1,2–Amino Alcohols via Catalytic Asymmetric Ring Opening of Meso Epoxides", J. Org. Chem. (1997) vol. 62, No. 12, pp. 4197–4199.
R. D. Sitrin, et al., "Aminoglycoside Antibiotics. 3. Synthesis of a Furanosyl Isomer of Kanamycin B from a Protected 3–Amino–3–deoxyglucofuranosyl Chloride", J. Org. Chem. (1978) vol. 43, No. 15, pp. 3048–3052.
S. E. Zook et al., "A concise synthesis of the HIV–protease inhibitor nelfinavir via an unusual tetrahydrofuran rearrangement", Tetrahedron Letters (2000), vol. 41, No. 36, pp. 7017–7021.

* cited by examiner

*Primary Examiner*—D. Margaret Seaman

(57) ABSTRACT

Methods for the preparation of chemical intermediates in the synthesis of HIV-protease inhibitors related to and including nelfinavir mesylate are disclosed. The method of this invention comprises converting tetrohydran derivatives into oxazolines to provide key reaction intermediates for the preparation of nelfinavir. Also disclosed is a method for the preparation of a chiral amino alcohol from an epoxytetrahydrofuran.

20 Claims, No Drawings

METHODS FOR THE PREPARATION OF INTERMEDIATES IN THE SYNTHESIS OF HIV-PROTEASE INHIBITORS

This application is a divisional of U.S. patent application Ser. No. 09/690,093, filed on Oct. 17, 2000, which claims the benefit of U.S. Provisional Application No. 60/160,695, filed on Oct. 21, 1999. Each of these applications are entirely incorporated herein by reference.

BACKGROUND OF THE INVENTION

1. Field of the Invention

This invention relates to chemical methods of preparing intermediates in the synthesis of the protease inhibitor nelfinavir mesylate and its free base, which is useful for treatment of HIV infected individuals.

2. Related Background Art

Treatment of HIV-infected individuals with HIV-protease inhibitors has emerged as an important method for preventing or inhibiting the rapid proliferation of the virus in human tissue. HIV-protease inhibitors block a key enzymatic pathway in the virus resulting in substantially decreased viral loads, which slows the steady decay of the immune system and its resulting deleterious effects on human health. The HIV-protease inhibitor nelfinavir mesylate has shown to be an effective treatment for HIV-infected individuals. Nelfinavir mesylate, and a method for its preparation are disclosed in U.S. Pat. No. 5,484,926, which is incorporated herein by reference.

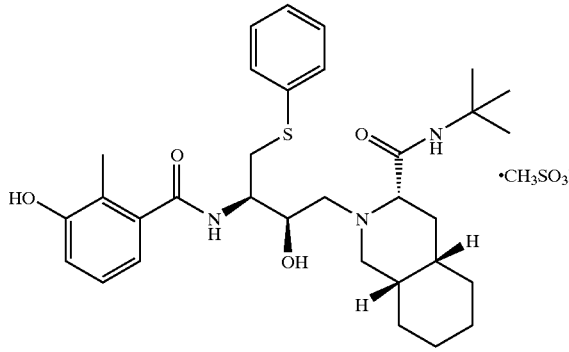

Other procedures for the preparation of nelfinavir mesylate and its free base have been reported. For example, PCT/JP96/02756 (WO97/11937) discloses the preparation of nelfinavir mesylate and its free base using oxazoline intermediates, which may be obtained from a 1,3-dioxepan-5-ol, or a derivative thereof. PCT/JP96/02757 (WO97/11938) discloses a related method, wherein the 1,3-dioxepan-5-ol is converted to nelfinavir mesylate and its free base via N-benzyloxycarbonyl-amino-butane diol intermediates. Each of these methods reportedly provide some improvement in the efficiency of the preparation of nelfinavir. However, further improvement would be desirable.

SUMMARY OF THE INVENTION

This invention relates to efficient and cost-effective methods for the preparation of nelfinavir mesylate and its free base. Specifically, the methods of this invention comprise the preparation of an oxazoline,

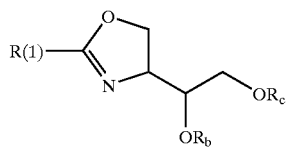

from a tetrahydrofuran

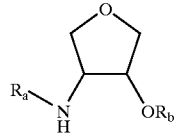

comprising treating the tetrahydrofuran, wherein $R_a$ is —COR(1) and $R_b$ is hydrogen, —COR(3), —SO$_2$R(2) or a suitable hydroxyl protecting group, with an oxophilic electrophilic reagent in a manner that is effective to provide the oxazoline, wherein $R_b$ is hydrogen, —COR(3), —SO$_2$R(2) or a suitable hydroxyl protecting group and $R_c$ is H, —COR(3) or —SO$_2$R(2); wherein R(1), R(2) and R(3) independently represent a substituted or unsubstituted alkyl, aryl, cycloalkyl, heterocycloalkyl or heteroaryl group. Advantageously, the methods of this invention provide nelfinavir mesylate and its free base in relatively high yield and employ fewer synthetic steps than the prior art methods.

This invention also relates to methods for making intermediate compounds that are useful in the method of preparation of nelfinavir mesylate and its free base. In addition, this invention relates to methods for the preparation of chiral starting materials that are useful in the methods for the preparation of nelfinavir mesylate and its free base according to this invention.

DETAILED DESCRIPTION OF THE INVENTION

This invention provides novel and useful methods for the conversion of amino-tetrahydrofuran derivatives to oxazoline intermediates that are useful in the preparation of nelfinavir mesylate and nelfinavir free base. All compounds of the inventive methods of this invention that contain at least one chiral center may exist as single stereoisomers, racemates and/or mixtures of enantiomers and/or diastereomers unless otherwise indicated. All such single stereoisomers, racemates and mixtures thereof are intended to be within the scope of this invention. Moreover, the scope of this invention is not intended to be limited to reactions of selected isomers. Although the reaction schemes described herein may be illustrated using compounds depicted as a single enantiomer or diastereomer, the methods of this invention are intended to encompass reactions of any isomer or racemic mixture of these compounds.

When used to describe a particular compound, the term "chiral" is used herein to indicate that the compound is substantially enantiomerically and/or diastereomerically pure, for example, as in the term "chiral amino-tetrahydrofuran." Compounds that are substantially enatiomerically pure contain at least 90% of a single isomer and preferably contain at least 95% of a single isomer. More preferably, the chiral compounds in this invention contain at least 97.5% of a single isomer and most preferably contain at least 99% of a single isomer. Compounds identified herein as single stereoisomers are meant to describe compounds that are present in a form that contains at least 90% of a single isomer. The term "racemic" or "racemic mixture" refers to a mixture of equal amounts of enantiomeric compounds, which encompasses mixtures of enantiomers and/or mixtures of enantiomeric diastereomers.

The method of this invention provides for the conversion of an amino-tetrahydrofuran, I, to an oxazoline, II, as illustrated below:

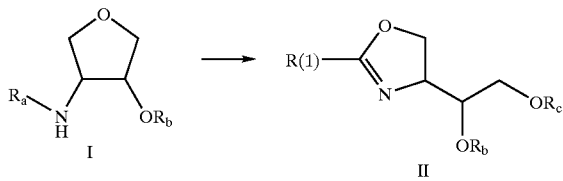

wherein
  $R_a$ is hydrogen or —COR(1)
  $R_b$ is hydrogen, —COR(3), —SO$_2$R(2) or a suitable hydroxyl protecting group;
  $R_c$ is hydrogen, —COR(3) or—SO$_2$R(2);
  wherein R(1), R(2) and R(3) independently represent a substituted or unsubstituted alkyl, aryl, cycloalkyl, heterocycloalkyl or heteroaryl group.

As used herein, the term "alkyl" represents a straight or branched chain alkyl group, preferably having one to eight, more preferably having one to six, and most preferably having from one to four carbon atoms. The term "$C_1$–$C_6$ alkyl" represents a straight or branched alkyl chain having from one to six carbon atoms. Exemplary $C_1$–$C_6$ alkyl groups include methyl, ethyl, n-propyl, isopropyl, butyl, isobutyl, sec-butyl, t-butyl, pentyl, neo-pentyl, hexyl, isohexyl, and the like. The term "$C_1$–$C_6$ alkyl" includes within its definition the term "$C_1$–$C_4$ alkyl."

The term "cycloalkyl" represents a group comprising a saturated or partially unsaturated, mono- or poly-carbocyclic ring, preferably having 5-14 ring carbon atoms. Exemplary cycloalkyls include monocyclic rings having from 3–7, preferably 3–6, carbon atoms, such as cyclopropyl, cyclobutyl, cyclopentyl, cyclopentenyl, cyclohexyl, cyclohexenyl, cycloheptyl and the like. An exemplary cycloalkyl is a $C_5$–$C_7$ cycloalkyl, which is a hydrocarbon ring structure containing from five to seven carbon atoms.

The term "aryl" represents a group comprising an aromatic, monovalent monocyclic, bicyclic, or tricyclic radical containing 6, 10, 14, or 18 carbon ring atoms, to which may be fused one or more cycloalkyl groups, heterocycloalkyl groups, or heteroaryl groups which may be unsubstituted or substituted by one or more of the substituents described below Illustrative examples of aryl groups include, but are not limited to, phenyl, napthyl, anthryl, phenanthryl, fluoren-2-yl, indan-5-yl, and the like.

The term "heterocycloalkyl" represents a group comprising a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms and which includes 1, 2, 3, 4, or 5 heteroatoms selected from nitrogen, oxygen and sulfur, and to which may be fused one or more cycloalkyl groups, aryl groups, or heteroaryl groups which may be unsubstituted or substituted by one ore more of the substituents described below. Illustrative examples of heterocycloalkyl groups include, but are not limited to azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo [2.2.1]heptyl, 1,5,9-triazacyclododecyl, and the like.

The term "heteroaryl" represents a group comprising an aromatic monovalent monocyclic, bicyclic, or tricyclic radical, containing 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, to which may be fused one or more cycloalkyl groups, heterocycloalkyl groups, or aryl groups, which may be unsubstituted or substituted by one or more of the substituents described below. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

In this invention, each of the above alkyl, aryl, cycloalkyl, heterocycloalkyl, or heteroaryl groups may be substituted by one or more substituents. If the substituents themselves are not compatible with the methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Green & P. Wuts, *Protective Groups in Organic Synthesis* (2nd Ed. 1991), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Exemplary substituents that may be present on an alkyl group include aryl, cycloalkyl, heterocycloalkyl, heteroaryl, nitro (NO$_2$), amino, alkylamino, dialkylamino, carbamoyl, alkylaminocarbonyl, dialkylaminocarbonyl, arylaminocarbonyl, dialkylamino, alkoxy, aryloxy, halogen, hydroxyl, alkanoyl, acyloxy, aroyl, aroyloxy, carboxyl, alkoxycarbonyl, aryloxycarbonyl, alkylcarbonylamino, arylcarbonylamino, mercapto, alkylthio, arylthio, wherein any of the aryl, cycloalkyl, heterocycloalkyl, heteroaryl moieties present in the above substituents may be further substituted by one or more of alkyl, aryl, nitro (NO$_2$), amino, halogen, hydroxyl, alkoxy, aryloxy, mercapto, alkylthio or arylthio. Exemplary substituents that may be present on the above aryl, cycloalkyl, heterocycloalkyl or heteroaryl groups include alkyl, aryl, cycloalkyl, heterocycloalkyl, heteroaryl, nitro (NO$_2$), amino, alkylamino, dialkylamino, carbamoyl, alkylaminocarbonyl, dialkylaminocarbonyl, arylaminocarbonyl, dialkylamino, alkoxy, aryloxy, halogen, hydroxyl, alkanoyl, acyloxy, aroyl, aroyloxy, carboxyl, alkoxycarbonyl, aryloxycarbonyl, alkylcarbonylamino, arylcarbonylamino, mercapto, alkylthio, arylthio, wherein any of the alkyl, aryl, cycloalkyl, heterocycloalkyl, heteroaryl moieties present in the above substituents may be further substituted by one or more of alkyl, aryl, nitro ($NO_2$), amino, halogen, hydroxyl, alkoxy, aryloxy, mercapto, alkylthio or arylthio.

The terms "halogen" and "halo" represent chloro, fluoro, bromo or iodo substituents.

Exemplary substituted alkyls include halo($C_1$–$C_4$)alkyl, which represents a straight or branched alkyl chain having from one to four carbon atoms with 1–3 halogen atoms attached to it. Exemplary halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, and the like. Another exemplary substituted alkyl is hydroxy ($C_1$–$C_4$)alkyl, which represents a straight or branched alkyl chain having from one to four carbon atoms with a hydroxy group attached to it. Exemplary hydroxy($C_1$–$C_4$)alkyl groups include hydroxymethyl, 2-hydroxyethyl, 3-hydroxypropyl, 2-hydroxyisopropyl, 4-hydroxybutyl, and the like. Yet another exemplary substituted alkyl is $C_1$–$C_4$ alkylthio($C_1$–$C_4$)alkyl, which is a straight or branched $C_1$–$C_4$ alkyl group with a $C_1$–$C_4$ alkylthio group attached to it. Exemplary $C_1$–$C_4$ alkylthio ($C_1$–$C_4$)alkyl groups include methylthiomethyl, ethylthiomethyl, propylthiopropyl, sec-butylthiomethyl, and the like. Another exemplary substituted alkyl is heterocycloalkyl($C_1$–$C_4$)alkyl or heteroaryl($C_1$–$C_4$)alkyl, which is a straight or branched alkyl chain having from one to four carbon atoms to which is attached a heterocycloalkyl or heteroaryl group. Exemplary heterocycloalkyl($C_1$–$C_4$) alkyl and heteroaryl($C_1$–$C_4$)alkyl groups include pyrrolylmethyl, quinolinylmethyl, 1-indolylethyl, 2-furylethyl, 3-thien-2-ylpropyl, 1-imidazolylisopropyl, 4-thiazolylbutyl and the like. Yet another exemplary substituted alkyl is aryl($C_1$–$C_4$)alkyl, which is a straight or branched alkyl chain having from one to four carbon atoms with an aryl group attached to it. Exemplary aryl($C_1$–$C_4$) alkyl groups include phenylmethyl (benzyl), 2-phenylethyl, 3-naphthyl-propyl, 1-naphthylisopropyl, 4-phenylbutyl and the like.

Exemplary substituted aryls include a phenyl or naphthyl ring substituted with one or more substituents, preferably one to three substituents, independently selected from halogen, hydroxyl, morpholino($C_1$–$C_4$)alkoxycarbonyl, pyridyl ($C_1$–$C_4$)alkoxycarbonyl, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N—($C_1$–$C_4$)alkylaminocarbonyl, amino, $C_1$–$C_4$alkylamino, di($C_1$–$C_4$)alkylamino or a group of the formula —$(CH_2)_a$—$R_7$ where a is 1, 2, 3 or 4 and $R_7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$) alkylamino.

Exemplary substituted heterocycloalkyls and heteroaryls may be substituted with 1,2 or 3 substituents independently selected from halogen, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N—($C_1$–$C_4$)alkylcarbamoyl N—($C_1$–$C_4$) alkylaminocarbonyl, amino, $C_1$–$C_4$alkylamino, di($C_1$–$C_4$) alkylamino or a group having the structure —$(CH_2)_a$—$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$alkylamino or di($C_1$–$C_4$)alkylamino.

Examples of substituted heterocycloalkyls include, but are not limited to, 3-N-t-butyl carboxamide decahydroisoquinolinyl and 6-N-t-butyl carboxamide octahydro-thieno[3,2-c]pyridinyl. Examples of substituted heteroaryls include, but are not limited to, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

In general terms, the conversion of a tetrahydrofuran, I, to an oxazoline, II, may be conducted by treatment of the tetrahydrofuran, wherein $RC_a$ is —COR(1) and $R_b$ is hydrogen, —COR(3), —$SO_2R(2)$ or a suitable hydroxyl protecting group, with an oxophilic electrophilic reagent that facilitates tetrahydrofuran ring-opening to provide the oxazoline, wherein $R_b$ is hydrogen, —COR(3), —$SO_2R(2)$ or a suitable hydroxyl protecting group and $R_c$ is hydrogen, —COR(3) or —$SO_2R(2)$. Accordingly, the hydroxyl protecting groups that may be suitable for use in the method of this invention (as $R_b$) include those hydroxyl protecting groups that are stable to the oxophilic electrophilic reagents or reagent combinations described herein. Suitable protecting groups and the methods for protecting and de-protecting hydroxyl substituents using such suitable protecting groups are well known to those skilled in the art; examples of which may be found in T. Green & P. Wuts, supra.

Typically, the first step in the method of this invention comprises the formation of the chiral tetrahydrofuran amide, B, from the known amino-tetrahydrofuran, A, using any suitable, conventional procedure. Examples of such conventional procedures may be found in T. Green & P. Wuts, supra, and include treatment with a suitable acid halide, R(1)COX, in the presence of a base, where X is a halogen, treatment with a suitable acid, R(1)COOH, in the presence of a suitable coupling reagent, e.g. dicyclohexylcarbodiimide, and the like. Preferably, this reaction is conducted using an acid chloride in the presence of triethylamine base.

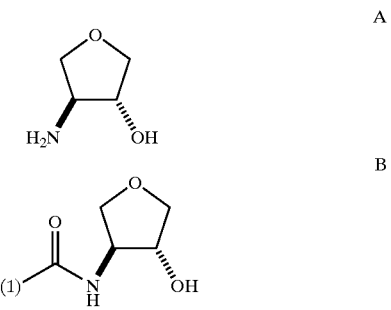

In one embodiment of this invention, the hydroxyl moiety of the chiral tetrahydrofuran amide, B, may be substituted by $R_b$, where $R_b$ is —$SO_2R(2)$ or a suitable protecting group, as defined above. Preferably, the hydroxyl moiety is converted to an alkyl or arylsulfonate (—$SO_2R(2)$), more preferably, a mesylate or tosylate. The methods for forming such— $OSO_2R(2)$ groups are well know in the art and may be accomplished using any suitable conventional procedure. Examples of such conventional procedures may also be found in T. Green & P. Wuts, supra. Preferably, this reaction is conducted using methanesulfonyl chloride or p-toluenesulfonyl chloride in the presence of triethylamine base.

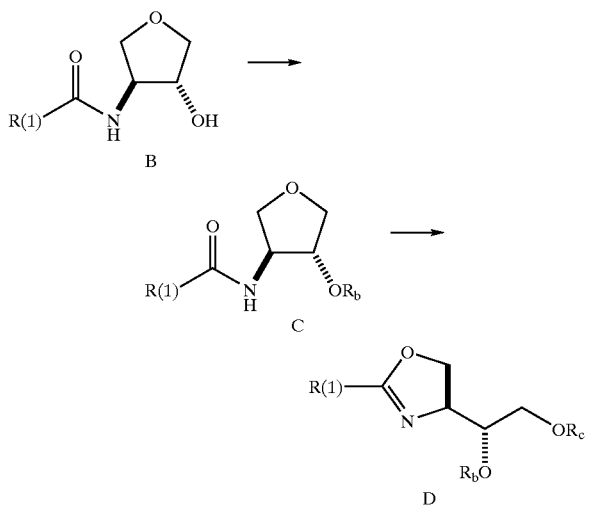

This hydroxy-substituted, chiral tetrahydrofuran amide, C, may then be converted to a chiral oxazoline, D. This conversion may be conducted using an oxophilic electrophilic reagent that facilitates tetrahydrofuran ring-opening and oxazoline ring-formation. As used herein the term "oxophilic electrophilic reagent" refers to a single reagent, or a set of reagents which when combined generate an oxophilic electrophilic intermediate, which facilitates tetrahydrofuran ring-opening and oxazoline ring-formation. Examples of oxophilic electrophilic reagents include, but are not limited to, suitable oxophilic Lewis acids (for example, metal halide Lewis acids, such as titanium tetrachloride, or strong oxophilic protic acids, such as trifluoromethanesulfonic acid (triflic acid)), a suitable acid anhydride, a combination of a suitable acid anhydride or a suitable acid halide with a suitable Lewis acid. Suitable anhydrides and acid halides include the anhydrides and acid halides (e.g., acid chlorides) of any conventional alkyl or aryl carboxylic or sulfonic acid as well as anhydrides of strong acids, for example, triflic anhydride. Suitable Lewis acids include well-known metal halide Lewis acids, such as titanium tetrachloride, aluminum trichloride and the like, and strong protic acids, such as sulfuric acid, nitric acid, phosphoric acid, trifluoroacetic acid, trifluoromethanesulfonic acid and the like. Generally, the reaction of the tetrahydrofuran-amide with an oxophilic electrophilic reagent to form the oxazoline may be conducted at a temperature of between −40° C. and 70° C. in aprotic solvents, including, but not limited to ethyl acetate, isopropyl acetate, dichloromethane, benzene and toluene, using about 1 to about 20 molar equivalents of the oxophilic electrophilic reagent (relative to the tetrahydrofuran-amide).

In the course of this reaction, the primary hydroxyl moiety formed on opening of the tetrahydrofuran may become substituted with the "cationic" moiety of the acid used in the reaction. When employing a Lewis acid or a strong protic acid as the oxophilic electrophilic reagent, the resulting oxazoline contains an unsubstituted primary hydroxyl moiety (where $R_c$ is H) either because the "cationic moiety" of the acid is $H_+$ or because the rapid hydrolysis of any intermediate formed using such reagents generates this product. The resulting hydroxyl moiety may be converted to into any art-recognized derivative using conventional techniques (e.g., an ether via alkylation, an ester via acylation, a carbonate by treatment with an alkyl- or aryl-oxycarbonyl chloride, or equivalent thereof, a carbamate by treatment with an isocyante, etc.).

For the preparation of nelfinavir and nelfinavir mesylate, the tetrahydrofuran amide is preferably converted to an oxazoline-ester derivative by treatment with an oxophilic electrophilic reagent comprising a suitable anhydride, for example, triflic anhydride, or with a combination of an anhydride or acid halide with a Lewis acid. Such reagents are capable of generating acylium ion intermediates and are well known in the art. For example, a suitable acylium intermediate may be prepared in situ by treatment of a suitable acid anhydride, optionally with a suitable protic acid, or by treatment of a suitable acid halide with a suitable Lewis acid. Suitable acid anhydrides, acid halides and Lewis acids are as described hereinabove. In the course of the reaction employing these reagents, the primary hydroxyl moiety formed on opening of the tetrahydrofuran becomes substituted with the alkyl or aryl carboxyl moiety of the anhydride or acid halide (illustrated as $R_c$ above, where $R_c$ is —COR(3), as defined above) used in the reaction. As exemplified herein, a useful oxophilic electrophilic reagent combination is comprised of acetic anhydride and sulfuric acid. Accordingly, in this embodiment of the method of this invention, the resulting oxazoline contains an acetylated primary hydroxyl moiety.

Generally, conversion of the tetrahydrofuran-amide to the oxazoline may be accomplished using an excess molar equivalent amount of each reagent of an oxophilic electrophilic reagent combination. This reaction may be conducted at a temperature of between −40° C. and 70° C. in aprotic solvents, including, but not limited to ethyl acetate, isopropyl acetate, dichloromethane, benzene and toluene, using about 1 to about 20 molar equivalents of a suitable acid and about 1 to about 20 molar equivalents of a suitable anhydride (relative to the tetrahydrofuran-amide) and using the acid anhydride and acid in a relative molar ratio of from about 1:5 to about 5:1 (anhydride:acid). Preferably, the conversion may be accomplished using an excess molar equivalent amount of the oxophilic electrophilic reagent, i.e., at least 2 to about 20 molar equivalents of the oxophilic electrophilic reagent. More preferably, the reaction may be conducted using about 2 to about 20 molar equivalents of acid and about 2 to about 20 molar equivalents of a suitable anhydride, wherein the ratio of anhydride to acid is from about 1:1 to about 5:1. For example, as exemplified herein, the conversion may be accomplished using 7.5 equivalents of a strong acid and 15 equivalents of an acid anhydride (i.e., wherein the ratio of anhydride to acid is 2:1 (in the range of from about 1.5:1 to about 3:1).

As described in PCT/JP96/02756 (WO97/11937), the disclosure of which is incorporated by reference herein, the resulting oxazoline, D, may be used for the preparation of intermediates, useful in the preparation of nelfinavir, especially Compounds 20 and 19,

20

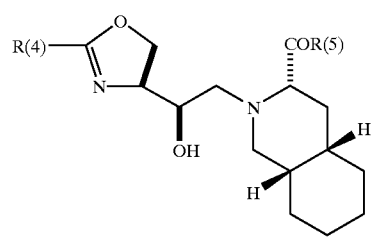

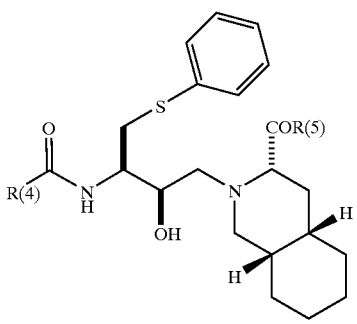

where R(4) is a substituted or unsubstituted alkyl, aryl, cycloalkyl, heterocycloalkyl, or heteroaryl group and R(5) is a substituted or unsubstituted NH-alkyl, NH-aryl, O-alkyl, or O-aryl group, wherein each alkyl or aryl moiety may be unsubstituted or substituted with the substituents described above.

Preferably, R(4) is

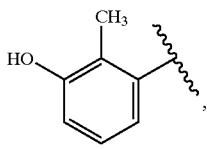

and R(5) is N-t-butyl.

In another embodiment of the method of this invention, the tetrahydrofuran-amide, B, may be directly converted to oxazoline, E. The amide may be treated in a manner similar to that described above. For example, the tetrahydrofuran-amide, B, may be treated directly with a suitable acid anhydride in the presence of a suitable acid, such as, for example, acetic anhydride and sulfuric acid, to form an oxazoline diester, E. Each hydroxyl moiety of the resulting oxazoline becomes substituted with the alkyl or aryl carboxyl moiety (illustrated as —COR(3), where R(3) is as defined above) of the anhydride used in the reaction. Accordingly, if acetic anhydride is used in this method, both hydroxyl moieties of the resulting oxazoline will be acetylated.

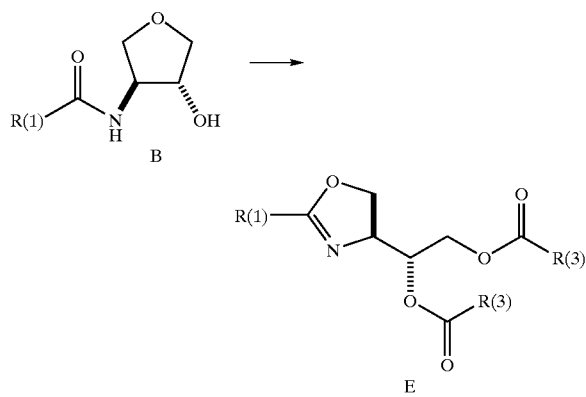

Each of the alkyl or aryl carboxyl moieties of oxazoline diester, E, may be removed (hydrolyzed to the corresponding hydroxyl moieties) using conventional procedures, for example, by treatment with a suitable base in a suitable solvent, to form the oxazoline diol, F. Bases that are suitable for effecting this hydrolysis are well known in the art and include potassium carbonate, sodium hydroxide, potassium hydroxide, and the like. Solvents that are suitable for this hydrolysis are similarly well known in the art and include, but are not limited to, lower alkanols (methanol, ethanol, isopropanol, etc.). Examples of other conventional procedures for the hydrolysis of esters may be found in T. Green & P. Wuts, supra.

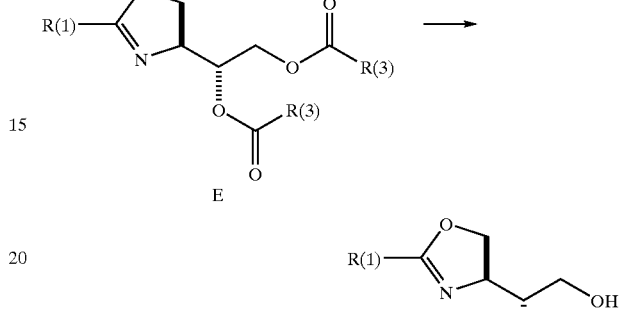

Conversion of the oxazoline diol, F, to nelfinavir via compound 19 may be conducted in a manner similar to that described in PCT/JP96/02757 (WO97/11938) for the conversion of 2(R), 3-dihydroxy-1(R)-phenylsulfanylmethyl-propyl)-carbamic acid benzyl ester to nelfinavir mesylate and its free base. The disclosure of PCT/JP96/02757 (WO97/11938) is incorporated by reference herein. For example, selective functionalization of the primary and secondary hydroxyl moieties of oxazoline diol, F, may be accomplished by first selectively protecting the primary hydroxyl moiety using a suitable hydroxyl protecting group. Suitable hydroxyl protecting groups and the methods for protecting and de-protecting hydroxyl substituents using such suitable protecting groups are well known to those skilled in the art; examples of which may be found in T. Green & P. Wuts, supra. Preferably, the primary hydroxyl moiety is protected as a para-nitrobenzoate ester. The secondary hydroxyl moiety may thereafter be functionalized by conversion to a leaving group. The term "leaving group" as used herein refers to any group that departs from a molecule in a substitution reaction by breakage of a bond. Examples of leaving groups include, but are not limited to, substituted or unsubstituted arylsulfonates and alkylsulfonates, prepared using a substituted or unsubstituted aryl or alkylsulfonyl halide. Preferably, the hydroxyl moiety is converted to a mesylate. This sulfonylated-protected oxazoline may then be converted to Compound 20 by addition of 3S,4aR,8aR-3-N-t-butylcarboxamidodecahydroisoquinoline (PHIQ), as described in PCT/JP96/02757.

In a preferred embodiment of the method of this invention, R(1) is

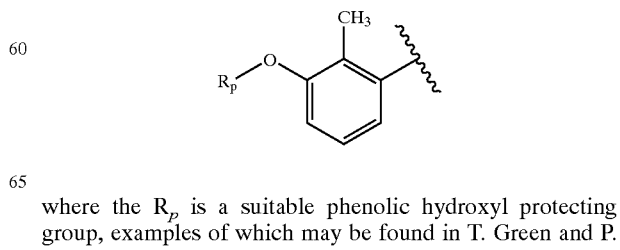

where the $R_p$ is a suitable phenolic hydroxyl protecting group, examples of which may be found in T. Green and P.

Wuts, supra. In a more preferred embodiment of this invention, R(1) is

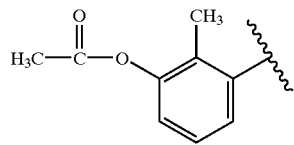

wherein the acetyl moiety used to protect the phenolic hydroxyl moiety is reactive to the hydrolysis conditions used to convert E to F. Accordingly, in this embodiment of the invention, oxazoline F is a triol, wherein R(1) is

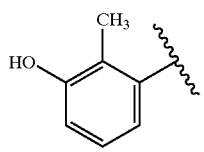

Selective functionalization of the phenolic, primary and secondary hydroxyl moieties of the oxazoline triol, may be accomplished by first selectively protecting the phenolic hydroxyl moiety using a suitable hydroxyl protecting group. Preferably, the phenolic hydroxyl moiety is protected as a para-nitrobenzoate ester. The primary hydroxyl moiety may then be protected using the same or different protecting group. If the same protecting groups is used, the phenolic and primary hydroxyl moieties may be protected in a single step. The secondary hydroxyl moiety may thereafter be functionalized by conversion to a mesylate. This sulfonylated-di-protected oxazoline may then be converted to Compound 20 by addition of 3S,4aR,8aR-3-N-t-butylcarboxamidodecahydroisoquinoline (PHIQ), in a manner similar to that described in PCT/JP96/02757.

This invention also provides a method for the preparation of a chiral tetrahydrofuran amide, wherein the 4-hydroxyl moiety possesses stereochemistry opposite to that of the chiral tetrahydrofuran amide, B, described hereinabove. This method comprises conversion of the tetrahydrofuran amide, B, to a fused tetrahydrofuranyloxazoline, G, by treatment with a substituted or unsubstituted sulfonylating reagent using two equivalents of a base. This reaction may be conducted at a temperature of between −78° C. and 100° C. in suitable solvents, including, but not limited to ethyl acetate, isopropyl acetate, toluene, benzene, dichloromethane, tetrahydrofuran, and the like.

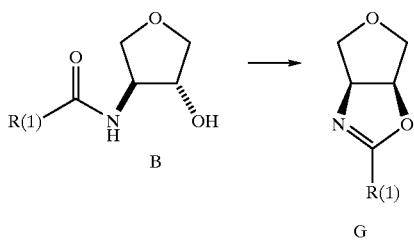

This fused heterocycle, G, may then be converted to chiral tetrahydrofuran amide, H, by treatment with aqueous acids, including, but not limited to, aqueous hydrochloric acid sulfuric acid, methanesulfonic acid, p-toluenesulfonic acid, phosphoric acid, and the like. This reaction may be conducted at a temperature of between −40° C. and 100° C. in suitable solvents, including, but not limited to water, alcoholic solvents, or mixtures thereof, where suitable alcoholic solvents include, but are not limited to lower alkanols, such as methanol, isopropanol, ethanol, and the like.

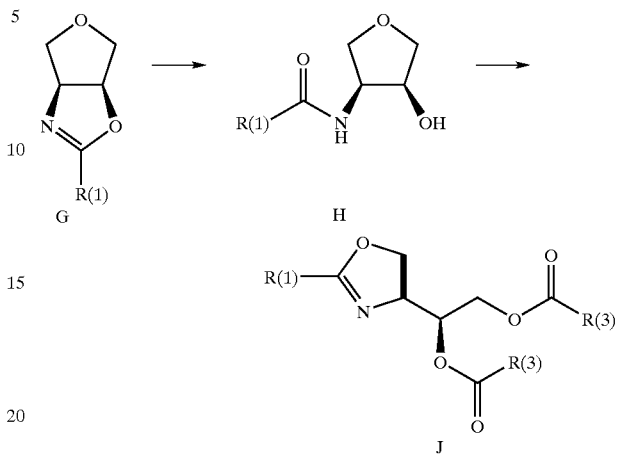

The tetrahydrofuran-amide, H, may be converted to the oxazoline diester, J, by treatment with an acid anhydride and an acid, according the methods described above. Hydrolysis of the alkyl or aryl carboxyl moieties of the oxazoline diester, J, to form diol, K, may also be accomplished according to the methods described above.

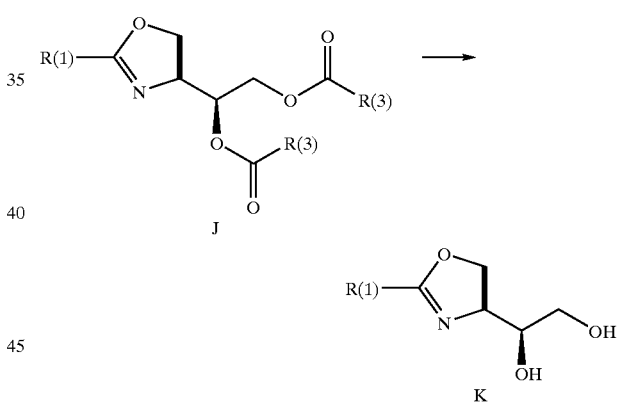

The primary hydroxyl moiety of the resulting oxazoline diol, K, may be functionalized by conversion to a leaving group, by treatment with a substituted or unsubstituted aryl or alkylsulfonyl halide, as described above. Preferably, the primary hydroxyl is converted to a tosylate or mesylate. Treatment of this functionalized oxazoline with a nucleophile, 3S,4aR,8aR-3-N-t-butylcarboxamidodecahydroisoquinoline (PHIQ) in the presence of a base, under conventional conditions, provides Compound 19. Conversion of Compound 19 into nelfinavir may be accomplished in a manner similar to that described in PCT/JP96/02757.

In another embodiment of this invention, the tetrahydrofuran-amide, H,

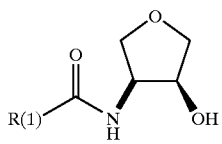

H may be converted to a protected tetrahydrofuran-amide, L, where R(10) may be any suitable hydroxyl protecting group.

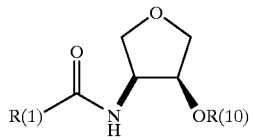

L

The protected tetrahydrofuran-amide, L, may then be converted directly to a protected oxazoline, M, by treatment with an oxophilic Lewis acid, an oxophilic protic acid, or triflic anhydride, wherein R(10) is any suitable protecting group for a hydroxyl moiety and R(11) is H or substituted alkyl sulfonyl.

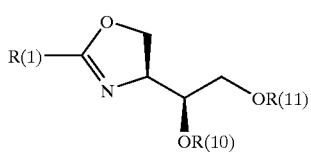

M

Conversion of the protected oxazoline, M, to nelfinavir may be conducted in a manner similar to that described hereinabove.

This invention further provides a method for the preparation of the chiral amino-tetrahydrofuran, A, or a salt thereof,

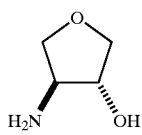

A comprising treating the achiral fused epoxy-tetrahydrofuran, N,

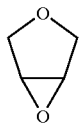

N with an amine reagent to form Compounds O or P, or a mixture thereof. This reaction may be conducted at a temperature of between −50° C. and 100° C. in suitable solvents, including, but not limited to alcoholic solvents, such as methanol, isopropanol, ethanol, and the like or aprotic solvents, such as isopropyl acetate, ethyl acetate, tetrahydrofuran, and the like.

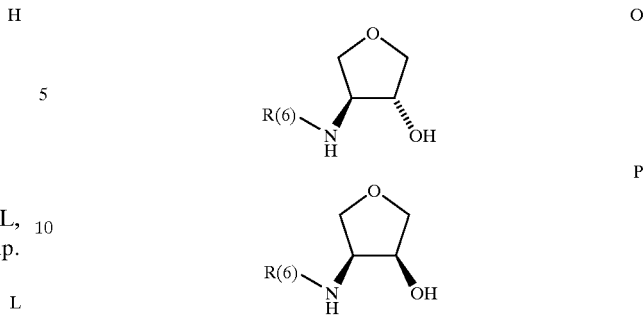

O

P

The amine reagent used in this method may be a chiral or an achiral aminating reagent. If the aminating reagent is chiral (i.e., R(6) is a chiral moiety), the mixture of amino-tetrahydrofurans formed is a diastereomeric mixture that may be treated using conventional techniques to provide separated amino-tetrahydrofuran diastereoisomers. After the isomers are separated, the chiral moiety of the chiral aminating reagent may be removed to provide each of the resolved amino-tetrahydrofuran enantiomers, or salts thereof. For the purposes of this separation, substituent R(6) is a suitable nitrogen protecting group that possesses a chiral center that is substantially enantiomerically pure. Preferably, R(6) is composed of at least 97.5% of a single isomer and more preferably, is composed of at least 99% of a single isomer. Moreover, the R(6) nitrogen protecting group must be removable under conditions that do not racemize the chiral amino-tetrahydrofuran, 1. Preferably, R(6) is a substantially enantiomerically pure substituted or unsubstituted alkanoyl, aroyl, arylalkylcarbonyl, arylalkyl or heteroarylalkyl, wherein the alkyl, aryl or heteroaryl moieties may be substituted with any of the alkyl, aryl or heteroaryl moieties described above. Most preferably, R(6) is

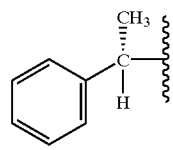

If the aminating reagent is achiral, for example, ammonia, the mixture of amino-tetrahydrofurans formed is an enantiomeric mixture that may be treated with a chiral reagent in a manner effective to provide a diastereomeric mixture of amino-tetrahydrofurans, wherein the chiral reagent contains a chiral auxiliary substituent. This diastereomeric mixture may be treated using conventional techniques to provide separated amino-tetrahydrofuran diastereoisomers. After the isomers are separated, the chiral auxiliary substituent may be separated from each of the separated amino-tetrahydrofurans to provide the resolved amino-tetrahydrofuran enantiomers, or salts thereof.

Exemplary techniques useful for the separation of stereoisomers are described in *Enantiomers, Racemates and Resolutions,* J. Jacques, A. Collet, S. Wilen, Krieger Pub. Co., (1991) Malabar, Fla., the disclosure of which is incorporated herein by reference. Examples of such separation techniques include crystallization, chromatography, and the like. Advantageously, the chiral amino-tetrahydrofuran prepared by this method is substantially enantiomerically pure, containing at least 90% of a single isomer and preferably containing at least 95% of a single isomer. More preferably, the chiral amino-tetrahydrofuran prepared by this method contains at least 97.5% of a single isomer and most preferably contains at least 99% of a single isomer.

Specifically, this invention provides a method for the preparation of:

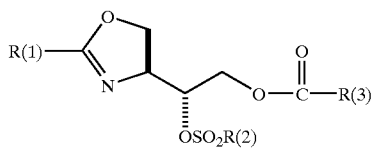

18 wherein R(11 ) is substituted or unsubstituted alkyl, aryl, cycloalkyl, heterocycloalkyl or heteroaryl, as defined above. Preferably, R(1) is a substituted or unsubstituted phenyl, or a substituted or unsubstituted $C_1$–$C_6$ alkyl. More preferably, R(1) is a substituted phenyl or $CF_3$.

Most preferably, R(1) is

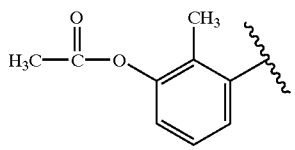

R(2) is a substituted or unsubstituted alkyl, aryl, cycloalkyl, heterocycloalkyl or heteroaryl. Preferably, R(2) is a substituted or unsubstituted alkyl or aryl. More preferably, R(2) is methyl, phenyl or tolyl. Most preferably, R(2) is methyl. R(3) is a substituted or unsubstituted alkyl, aryl, cycloalkyl, heterocycloalkyl or heteroaryl. Preferably, R(3) is a substituted or unsubstituted alkyl or aryl. More preferably, R(3) is methyl or phenyl. Most preferably, R(3) is methyl.

A preferred embodiment of this method comprises the steps of:

(1) treating amino-tetrahydrofuran, 1, or a salt thereof,

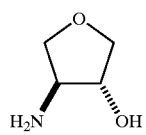

1 in a manner that is effective to convert the amino-tetrahydrofuran, 1, or a salt thereof, to tetrahydrofuran-amide, 2,

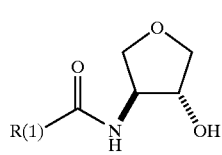

2

(2) treating tetrahydrofuran-amide, 2, in a manner that is effective to convert the tetrahydrofuran-amide, 2, to tetrahydrofuran amide-sulfonate, 3,

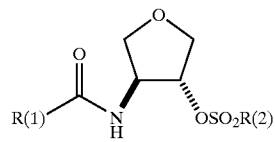

3 comprising the step-wise treatment of tetrahydrofuran-amide, 2, with at least one molar equivalent amount of a sulfonylating reagent, followed by treatment with a base, wherein the molar equivalent amount of base used in the treatment is less than the molar equivalent amount of the sulfonylating reagent, and (3) treating tetrahydrofuran amide-sulfonate, 3, in a manner that is effective to convert the tetrahydrofuran amide-sulfonate, 3, to the oxazoline, 18.

Preferably, tetrahydrofuran-amide, 2, may be treated first with a substituted or unsubstituted alkyl or aryl sulfonyl chloride, followed by treatment with less than a molar equivalent amount (with respect to the amount of sulfonyl chloride) of a base, in a manner effective to convert the tetrahydrofuran-amide, 2, to tetrahydrofuran amide-sulfonate, 3, and tetrahydrofuran amide-sulfonate, 3, may be treated with an oxophilic electrophilic reagent in a manner that is effective to convert the tetrahydrofuran amide-sulfonate, 3, to the oxazoline, 18.

This invention also provides a method for the preparation of Compound 19:

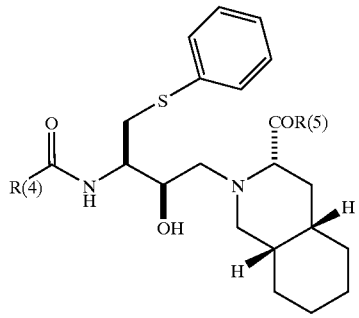

wherein R(4) is a substituted or unsubstituted alkyl, aryl, cycloalkyl, heterocycloalkyl, or heteroaryl group and R(5) is a substituted or unsubstituted NH-alkyl, NH-aryl, O-alkyl, or O-aryl group, wherein each alkyl or aryl moiety may be substituted or unsubstituted with the substituents described above. Most preferably, R(4) is

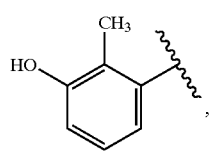

and R(5) is N-t-butyl.

This method is comprised of the following steps:

(1) treating amino-tetrahydrofuran, 1, or a salt thereof,

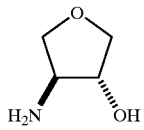

1 in a manner that is effective to convert the amino-tetrahydrofuran, 1, or a salt thereof, to tetrahydrofuran-amide, 2,

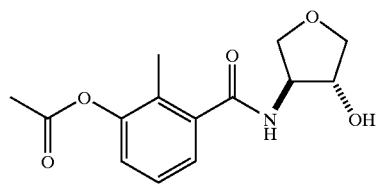

2

(2) treating tetrahydrofuran-amide, 2, in a manner that is effective to convert the tetrahydrofuran-amide, 2 to tetrahydrofuran amide-sulfonate, 3,

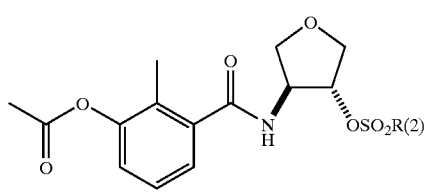

3 comprising the step-wise treatment of tetrahydrofuran-amide, 2, with at least one molar equivalent amount of a sulfonylating reagent, followed by treatment with a base, wherein the molar equivalent amount of base used in the treatment is less than the molar equivalent amount of the sulfonylating reagent, and (3) treating tetrahydrofuran amide-sulfonate, 3, in a manner that is effective to convert the tetrahydrofuran amide-sulfonate, 3, to the oxazoline, 18,

18

(4) treating oxazoline, 18, in a manner that is effective to convert the oxazoline, 18, to Compound 20,

20 and (5) treating Compound 20 in a manner that is effective to convert Compound 20 to Compound 19.

Preferably, tetrahydrofuran-amide, 2, may be treated first with a substituted or unsubstituted alkyl or aryl sulfonyl chloride, followed by treatment with less than a molar equivalent amount (with respect to the amount of sulfonyl chloride) of a base, in a manner effective to convert the tetrahydrofuran-amide, 2, to tetrahydrofuran amide-sulfonate, 3, and tetrahydrofuran amide-sulfonate, 3, may be treated with an oxophilic electrophilic reagent in a manner that is effective to convert the tetrahydrofuran amide-sulfonate, 3, to the oxazoline, 18; oxazoline 18 may be treated with 3S,4aR,8aR-3-N-t-butylcarboxamidodecahydroisoquinoline in a manner that is effective to convert oxazoline 18 to Compound 20, which maybe converted to Compound 19, according to the procedures described in PCT/JP96/02756 (WO97/11937).

Another method of this invention comprises the method for the preparation of Compound 20:

20 comprising the steps of:

(1) treating amino-tetrahydrofuran, 1, or a salt thereof,

1 in a manner that is effective to convert the amino-tetrahydrofuran, 1, or a salt thereof, to tetrahydrofuran-amide, 2,

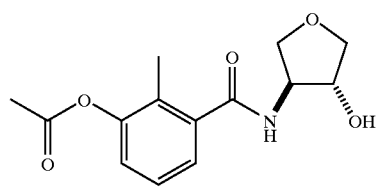

(2) treating tetrahydrofuran-amide, 2, in a manner that is effective to convert the tetrahydrofuran-amide, 2, to oxazoline triester, 4,

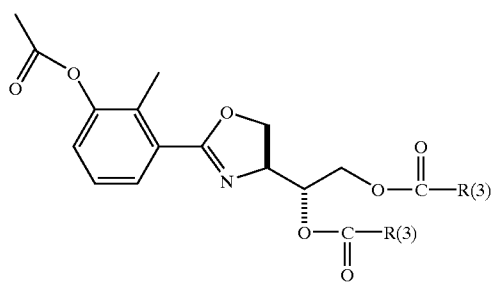

(3) treating oxazoline triester, 4, in a manner that is effective to convert the oxazoline triester, 4, to oxazoline triol, 5,

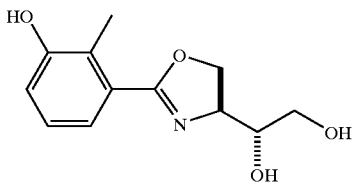

(4) treating oxazoline, 5, in a manner that is effective to convert the oxazoline triol, 5, to Compound 6 or Compound 7,

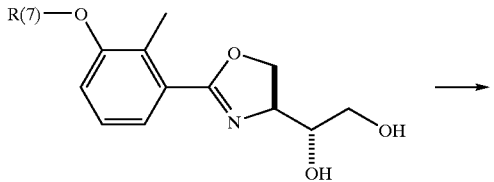

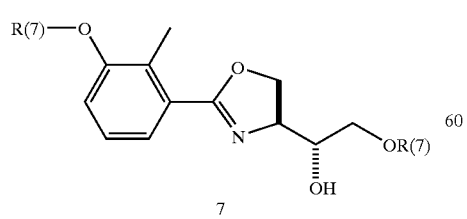

(5) treating Compound 7 in a manner that is effective to convert Compound 7 to Compound 8,

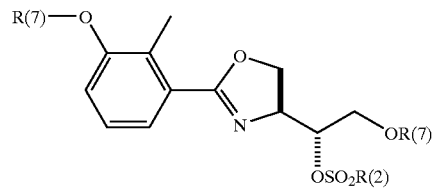

(6) treating Compound 8 in a manner that is effective to convert Compound 8 to Compound 20;

wherein R(7) is any suitable protecting group for a hydroxyl moiety. Suitable hydroxyl protecting groups and the methods for protecting and de-protecting hydroxyl substituents using such suitable protecting groups are well known to those skilled in the art; examples of which may be found in T. Green & P. Wuts, supra. Preferably, R(7) is trialkylsilyl, dialkyl-monoarylsilyl, diaryl-monoalkylsilyl, substituted or unsubstituted aroyl or alkanoyl. Preferably, R(7) is trimethylsilyl, tert-butyldimethylsilyl, benzoyl, para-nitrobenzoyl, triisopropylsilyl, and the like. Most preferably, R(7) is a para-nitrobenzoyl (PNB) moiety.

Preferably, tetrahydrofuran-amide, 2, may be treated with an oxophilic electrophilic reagent in a manner that is effective to convert the tetrahydrofuran-amide, 2, to oxazoline triester, 4. Oxazoline triester, 4, may be hydrolyzed to oxazoline triol, 5. The phenolic hydroxyl moiety of oxazoline triol, 5, may be protected with a suitable hydroxyl protecting group, in a manner that is effective to convert the oxazoline triol, 5, to protected oxazoline, 6. Alternatively, both the phenolic and primary hydroxyl moieties of oxazoline triol, 5, may be protected with a suitable hydroxyl protecting group, in a manner that is effective to convert the oxazoline triol, 5, to di-protected oxazoline, 7. Di-protected oxazoline, 7, may be treated with a substituted or unsubstituted alkyl or aryl sulfonylating reagent, in a manner that is effective to convert the oxazoline, 7, to a sulfonylated-di-protected oxazoline, 8. The sulfonylated-di-protected oxazoline, 8, may be treated with 3S,4aR,8aR-3-N-t-butylcarboxamidodecahydroisoquinoline in a manner that is effective to convert the oxazoline, 8, to Compound 20.

Yet another method according to this invention comprises a method for the preparation of Compound 19:

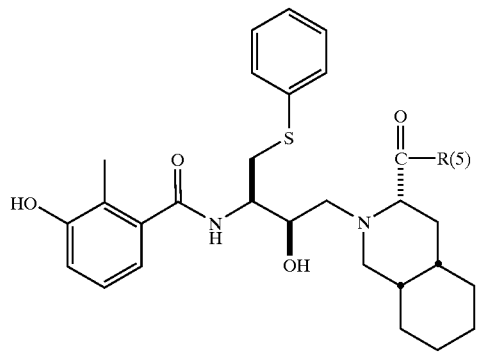

This method comprises the steps of:
(1) converting amino-tetrahydrofuran, 1,

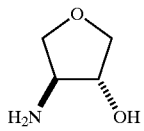

1 or a salt thereof to tetrahydrofuran-amide, 2,

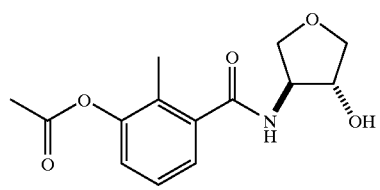

2

(2) converting tetrahydrofuran-amide, 2, to oxazoline triester, 4,

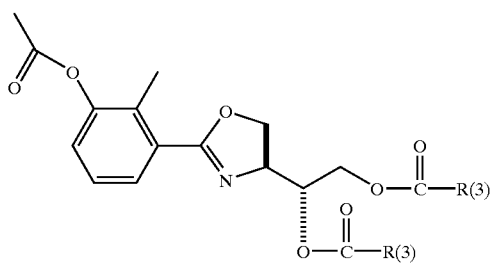

4

(3) converting oxazoline triester, 4 to oxazoline triol 5,

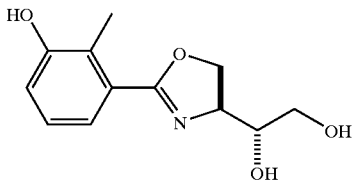

5

(4) converting oxazoline triol, 5 to di-protected oxazoline, 7;

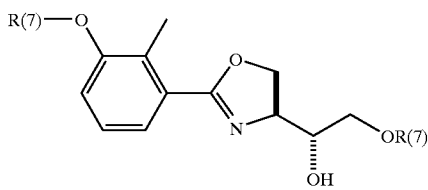

7 wherein the di-protected oxazoline, 7, may be converted to nelfinavir via Compound 19 using the method described in PCT/JP96/02757.

For example, the di-protected oxazoline, 7, may be converted to Compound 19 by the method comprising the steps of:
(1) converting di-protected oxazoline, 7, to sulfonylated-di-protected oxazoline, 8,

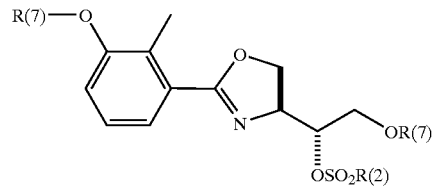

8

(2) converting the sulfonylated-di-protected oxazoline, 8, to Compound 20,

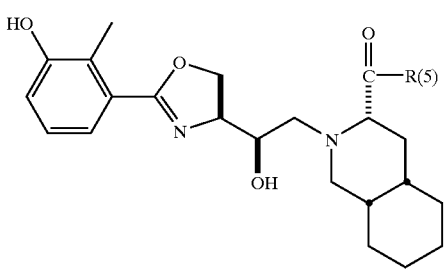

20 and
(3) converting Compound 20 to Compound 19.

Preferably, tetrahydrofuran-amide, 2, may be treated with an oxophilic electrophilic reagent in a manner that is effective to convert the tetrahydrofuran-amide, 2, to oxazoline triester, 4. Oxazoline triester, 4, may be hydrolyzed to oxazoline triol, 5. The phenolic and primary hydroxyl moieties of oxazoline triol, 5, may be protected with a suitable hydroxyl protecting group, in a manner that is effective to convert the oxazoline triol, 5, to di-protected oxazoline, 7. The di-protected oxazoline, 7, may be treated with a substituted or unsubstituted alkyl or aryl sulfonylating reagent, in a manner that is effective to convert the oxazoline, 7, to a sulfonylated-di-protected oxazoline, 8. The sulfonylated-di-protected oxazoline, 8, may be treated with 3S,4aR,8aR-3-N-t-butylcarboxamidodecahydroisoquinoline in a manner that is effective to convert the oxazoline, 8, to Compound 20.

Still another method according to this invention relates to a method for the preparation of Compound 19:

19 wherein the method comprises the steps of:
(1) converting amino-tetrahydrofuran, 1, or a salt thereof to tetrahydrofuran-amide,
(2) converting tetrahydrofuran-amide, 2, to fused tetrahydrofuranyloxazoline, 9,

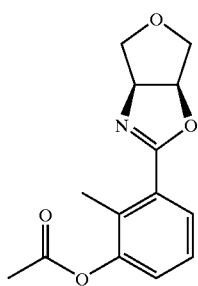

9

(3) converting the fused tetrahydrofuranyloxazoline, 9, to tetrahydrofuran-amide, 10,

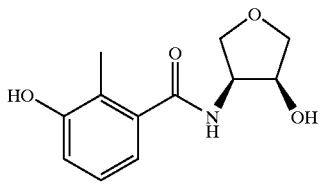

10

(4) converting the tetrahydrofuran-amide, 10, to an oxazoline triester, 11,

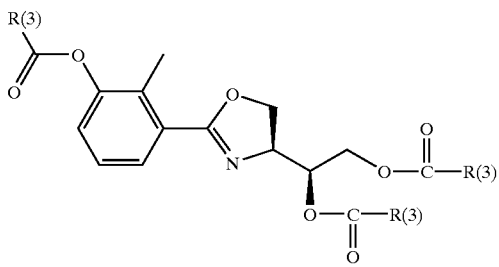

11

(5) converting the oxazoline triester, 11, to oxazoline triol, 12,

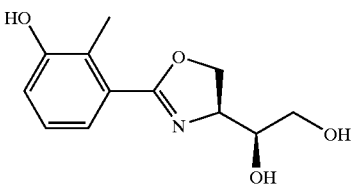

12

(6) converting the oxazoline triol, 12, to a functionalized oxazoline, 13,

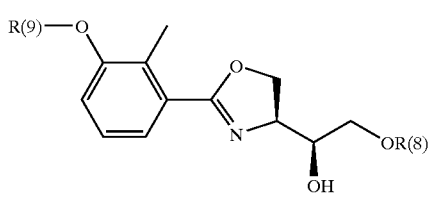

13 wherein R(8) together with the oxygen to which it is attached forms a suitable leaving group and R(9) is H or R(8), (7) converting the functionalized oxazoline, 13, to Compound 20,

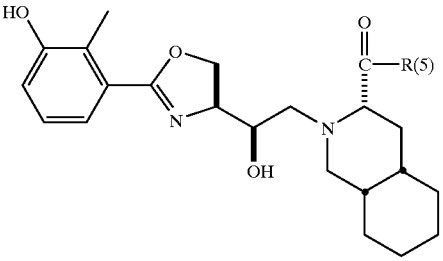

20

(8) converting Compound 20 to Compound 19,

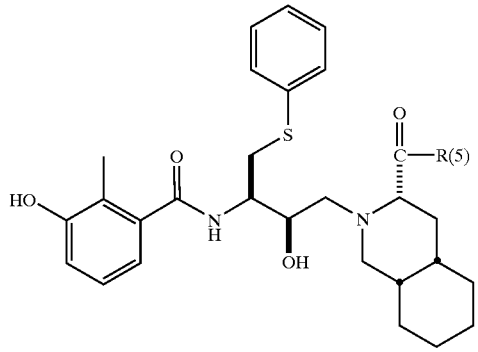

19

Preferably, tetrahydrofuran-amide, 2, may be treated with a substituted or unsubstituted alkyl or aryl sulfonylating reagent, in a manner effective to convert the tetrahydrofuran-amide, 2, to fused tetrahydrofuranyloxazoline, 9. The fused tetrahydrofuranyloxazoline, 9, may be hydrolyzed to tetrahydrofuran-amide, 10. Tetrahydrofuran-amide, 10, may be treated with an oxophilic electrophilic reagent in a manner that is effective to convert the tetrahydrofuran-amide, 10, to oxazoline triester, 11. Oxazoline triester, 11, may be hydrolyzed to oxazoline triol, 12. Oxazoline triol, 12, may be functionalized by treatment with a substituted or unsubstituted alkyl or aryl sulfonylating reagent in a manner effective to convert oxazoline, 12, to a functionalized sulfonylated oxazoline, 13. Oxazoline, 13, may be treated with 3S,4aR,8aR-3-N-t-butylcarboxamidodecahydroisoquinoline in a manner that is effective to convert the oxazoline to Compound 20.

Another method of this invention comprises the method for the preparation of Compound 20:

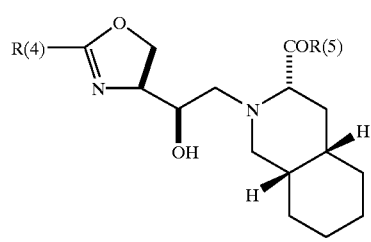

20 comprising the steps of:
(1) treating amino-tetrahydrofuran, 1, or a salt thereof,

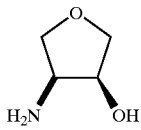

in a manner that is effective to convert the amino-tetrahydrofuran, 1, or a salt thereof, to tetrahydrofuran-hydroxy-amide, 10,

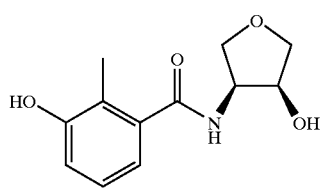

(2) treating tetrahydrofuran-hydroxy-amide, 10, in a manner that is effective to protect the hydroxyl moiety of the tetrahydrofuran-amide, 10, to form a protected tetrahydrofuran-amide, 21,

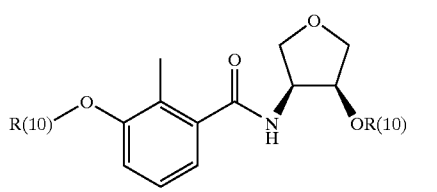

(3) treating the protected tetrahydrofuran-amide, 21, in a manner that is effective to convert the tetrahydrofuran-amide, 21, to a protected oxazoline, 22,

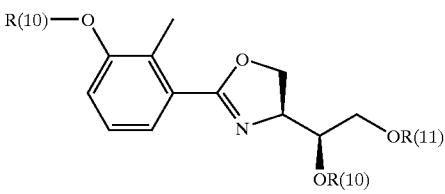

(4) treating protected oxazoline, 22, in a manner that is effective to convert the oxazoline, 22, to Compound 20; wherein R(10) is any suitable protecting group for a hydroxyl moiety and R(11) is H or substituted alkyl sulfonyl.

Suitable R(10) hydroxyl protecting groups and the methods for protecting and de-protecting hydroxyl substituents using such suitable protecting groups are well known to those skilled in the art; examples of which may be found in T. Green & P. Wuts, supra.

Preferably, the hydroxyl moiety of tetrahydrofuran-amide, 10, may be protected with a suitable hydroxyl protecting group, in a manner that is effective to convert the tetrahydrofuran-amide, 10, to a protected tetrahydrofuran-amide, 21, where R(10) is any suitable protecting group. The protected tetrahydrofuran-amide, 21, may be treated with an oxophilic electrophilic reagent in a manner that is effective to convert the protected tetrahydrofuran-amide, 21, to a protected oxazoline, 22. Preferably, the tetrahydrofuran-amide, 21, is treated with an oxophilic Lewis acid, an oxophilic protic acid, or triflic anhydride.

Another method of the invention relates to a method for preparing a chiral amino-tetrahydrofuran, 1, or a salt thereof in substantially diastereomerically pure form.

The method comprises the steps of: (1) converting fused epoxy-tetrahydrofuran, 14,

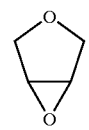

to a stereoisomeric mixture of amino-tetrahydrofurans,
(2) treating the stereoisomeric mixture of amino-tetrahydrofurans in a manner effective to resolve the amino-tetrahydrofuran stereoisomers, and
(3) isolating the resolved stereoisomers of amino-tetrahydrofuran, 1 and 1', or a salt thereof

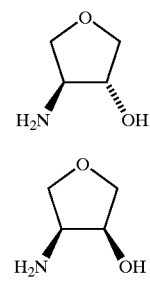

The epoxy-tetrahydrofuran, 14, may be treated with an aminating reagent to form the stereoisomeric mixture of amino-tetrahydrofurans, 1 and 1'.

As described herein, the compounds of this invention may be used as salts. The salts may be pharmaceutically acceptable salts. The term "pharmaceutically acceptable salt" refers to those salts that retain the biological effectiveness and properties of the free acids and bases and/or that are not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, nitrobenzoates, dinitrobenzoates, hydroxybenzoates, methoxybenzoates, phthalates, sulfonates, phenylsulfonates, toluenesulfonates, methanesulfonates, propanesulfonates, naphthalene-1-sulfonates, naphthalene-2-sulfonates, phenylacetates, phenylpropionates, phenylbutyrates, citrates, lactates, hydroxybutyrates, glycolates, tartrates and mandelates. Although any pharmaceutically acceptable salt of the compounds described hereinabove may be prepared, preferred salts are p-toluenesulfonate salts.

If a compound of an inventive method of this invention is a base, the desired salt may be prepared by any suitable method known to the art, including treatment of the free base with an acid. Such treatment provides the salt as a protonated base, together with a counterion, which may include, but is not limited to, inorganic ions, such as halogens, pseudohalogens, sulfates, hydrogen sulfates, nitrates, hydroxides, phosphates, hydrogen phosphates, dihydrogen phosphates, perchlorates, and related complex inorganic anions, and organic ions, such as carboxylates, sulfonates, bicarbonates and carbonates. Exemplary acids useful in the method of this invention include inorganic acids, such as hydrochloric acid, hydrobromic acid, sulfuric acid, nitric acid, phosphoric acid and the like, and organic acids, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such as p-toluenesulfonic acid, phenylsulfonic acid or methanesulfonic acid, or the like.

If a compound of an inventive method of this invention is an acid, the desired salt may be prepared by any suitable method known to the art, including treatment of the free acid with an inorganic or organic base, such as an amine (primary, secondary or tertiary), or an alkali metal or alkaline earth metal hydroxide or the like. Illustrative examples of suitable salts include organic salts derived from amino acids such as glycine and arginine, ammonia, primary, secondary and tertiary amines, cyclic amines such as piperidine, morpholine and piperazine, and inorganic salts derived from sodium, calcium, potassium, magnesium, manganese, iron, copper, zinc, aluminum, and lithium.

This invention also provides novel and useful methods for producing intermediates that are especially useful in the preparation of nelfinavir mesylate and nelfinavir free base. Particularly useful intermediates are Compounds 19' and 20'. As illustrated below, these compounds may be prepared from chiral tetrahydrofuran Compounds 1' or 2'.

Compound 18' may be prepared by the reaction sequence illustrated in Scheme I, below. In this embodiment of the method of this invention, chiral amino-tetrahydrofuran, 1', is treated with 3-acetoxy-2-methylbenzoyl chloride (AMBC) under conditions effective to form an amide, (12-acetoxy-3-methyl benzamide, 2') or a salt thereof. The resulting amide, tetrahydrofuran-amide, 2', may be treated with methanesulfonyl chloride in the presence of a base, such as, for example, triethylamine, under conditions effective to derivatize the secondary alcohol of tetrahydrofuran-amide, 2', providing an intermediate mesylate tetrahydrofuran amide-sulfonate, 3', which need not be isolated. For example, this reaction may be conducted by first treating tetrahydrofuran 2' with at least one molar equivalent of methanesulfonyl chloride, followed by addition of less than a molar equivalent amount (with respect to the amount of methanesulfonyl chloride) of triethylamine. Tetrahydrofuran amide-sulfonate, 3', may then be treated with an anhydride, such as, for example, acetic anhydride, and a strong acid, such as, for example, sulfuric acid, under conditions effective to produce Compound 18'. For example, tetrahydrofuran amide-sulfonate, 3', may be treated with 15 molar equivalents of acetic anhydride and 7.5 molar equivalents of a strong acid, such as, for example, sulfuric acid, to produce Compound 18'. Other strong acids useful in this treatment step include trifluoromethanesulfonic acid, nitric acid, phosphoric acid, and the like.

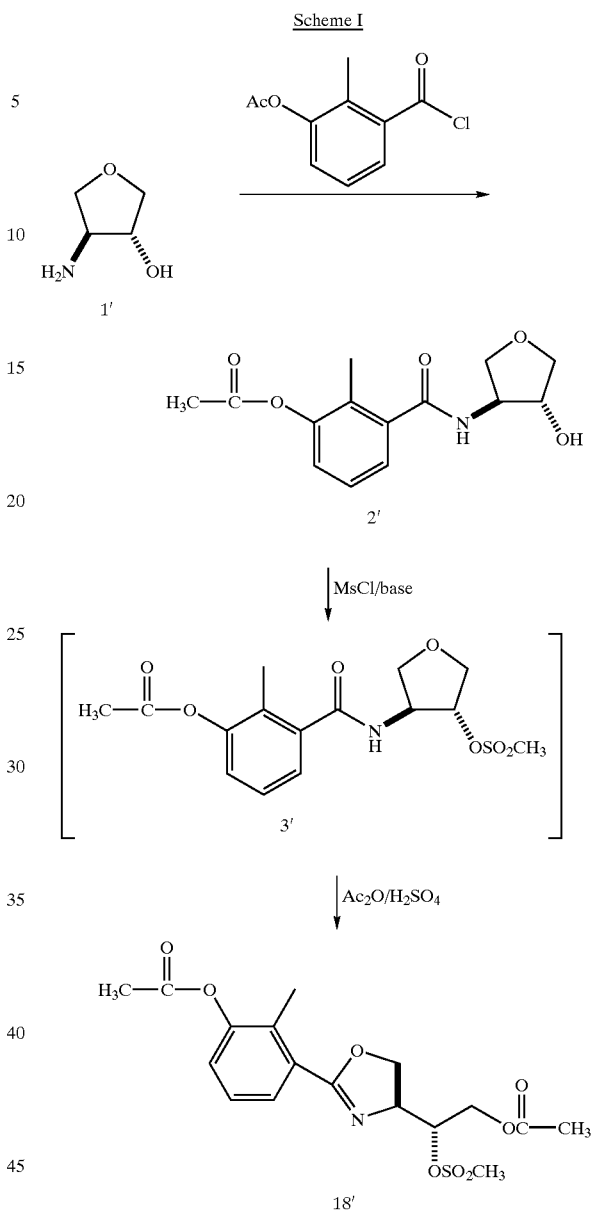

It is considered within the ordinary skill of one in the art through routine experimentation to determine the reaction conditions (solvent, reaction time, temperature, etc.) that are effective to produce all of the compounds, described herein. For example, the above-described reactions for the conversion of amino-tetrahydrofuran, 1', to Compound 19', using the moisture-sensitive acid chloride, AMBC, and sulfonyl chloride, mesylchloride, would preferably be conducted in an aprotic solvent (i.e., one that is not water or an alcohol). Preferably, the aprotic solvent is an aprotic solvent, e.g. ethyl acetate, isopropyl acetate, toluene, benzene and the like.

The preparation of Compound 20', as illustrated in the reaction sequence of Scheme II, below, may also be prepared from the amino-tetrahydrofuran, 1', or a pharmaceutically acceptable salt thereof. As in the above-described reaction sequence, the first step of this sequence involves the formation of the amide intermediate, tetrahydrofuran-amide, 2'. This amide intermediate may be treated directly with an anhydride, such as, for example, acetic anhydride, and a strong acid, such as, for example, sulfuric acid, to form oxazoline triester, 4'. Each of the acetoxy moieties of oxazoline triester, 4', may be removed (hydrolyzed to the corresponding hydroxyl moieties), by treatment with a suitable base in a suitable solvent, to form the oxazoline triol, 5'. Bases that are suitable for effecting this hydrolysis are known in the art and include potassium carbonate, sodium hydroxide, potassium hydroxide, and the like. Solvents that are suitable for effecting this hydrolysis are similarly known in the art and include lower alkanols (methanol, ethanol, isopropanol, etc.).

Advantageously, the phenolic, primary and secondary hydroxyl moieties of oxazoline triol, 5' may be selectively protected, as illustrated below. For example, the phenolic hydroxyl moiety may be protected as the p-nitrobenzoate, Compound 6', using p-nitrobenzoyl chloride. The primary hydroxyl moiety of Compound 6' may then be selectively protected using the same or a different protecting group. Alternatively, both the phenolic and primary hydroxyl moieties of oxazoline triol, 5', may be protected using p-nitrobenzoyl chloride to form the di-p-nitrobenzoate, Compound 7'. This process may be conducted in a single step, using two equivalents of p-nitrobenzoyl chloride, or in a stepwise process, as described above.

As illustrated in Scheme III, treating Compound 7' with methanesulfonyl chloride (although another substituted or unsubstituted alkyl or aryl sulfonyl chloride may be used) in the presence of a base, such as, for example, triethylamine, provided Compound 8', which may be converted into Compound 20' by addition of 3S,4aR,8aR-3-N-t-butylcarboxamidodecahydroisoquinoline (PHIQ) in the presence of potassium carbonate and methanol. Further treatment with thiophenol provided nelfinavir. Treatment of Compound 7' with the sulfonyl chloride and base may be conducted using conventional conditions.

Scheme III

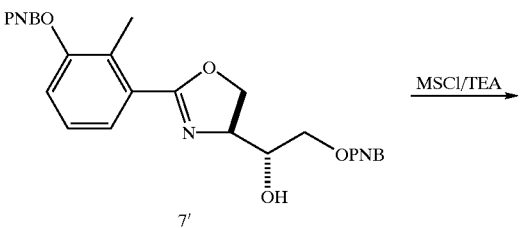

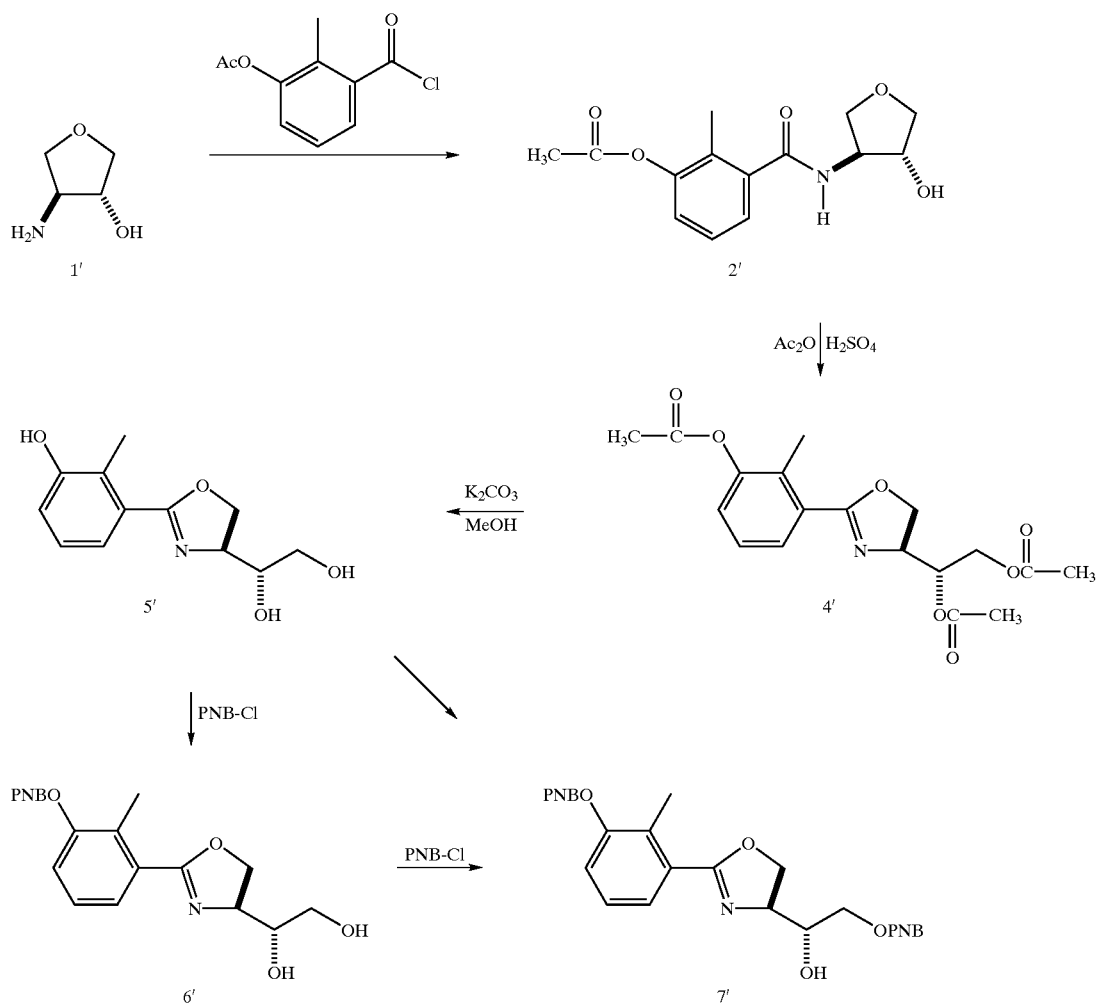

31
-continued

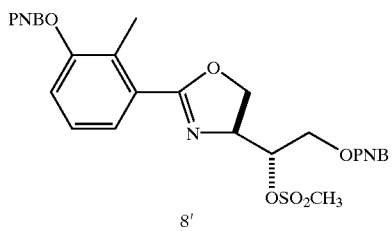

8'

PHIQ | K₂CO₃/MeOH ↓

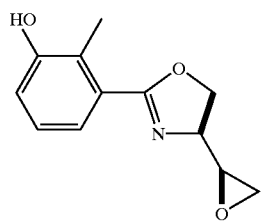

epoxide intermediate

↓

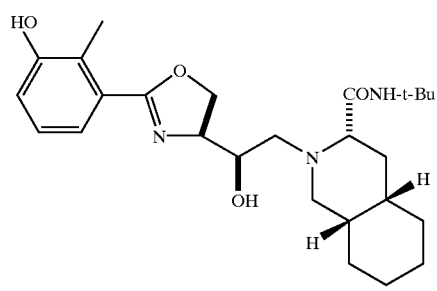

20'

PhSH ↓

32
-continued

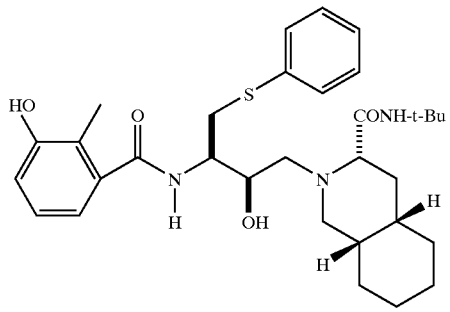

19'

An alternative reaction sequence for preparing Compound 19' beginning with the formation of tetrahydrofuran-amide, 2', from amino-tetrahydrofuran, 1', comprises the formation of the fused tetrahydrofuranyloxazoline, 9', as illustrated in Scheme IV, below. Treatment of the tetrahydrofuran-amide, 2', with methanesulfonyl chloride (although another substituted or unsubstituted alkyl or aryl sulfonyl chloride may be used) in the presence of a base, such as, for example, triethylamine, provides the novel fused tetrahydrofuranyloxazoline, 9'. Acid treatment of this oxazoline provides the tetrahydrofuran-amide, 10', wherein the stereochemistry of the 4-hydroxyl moiety is opposite that of the starting tetrahydrofuran, 2'. Treatment of the tetrahydrofuran-amide, 10', with acetic anhydride in the presence of a strong acid, such as sulfuric or nitric acid, affords Compound 11', a triacetate. Hydrolysis of this triacetate provides triol, 12'.

Scheme IV

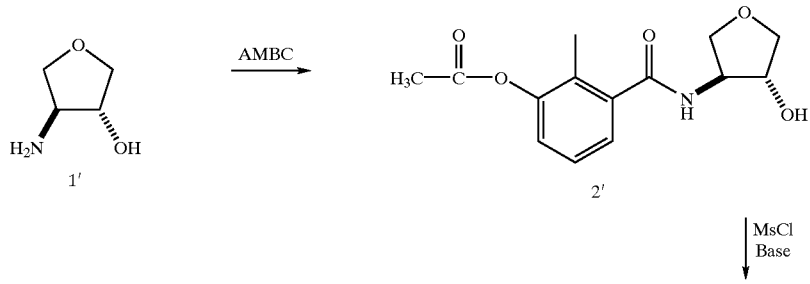

MsCl Base ↓

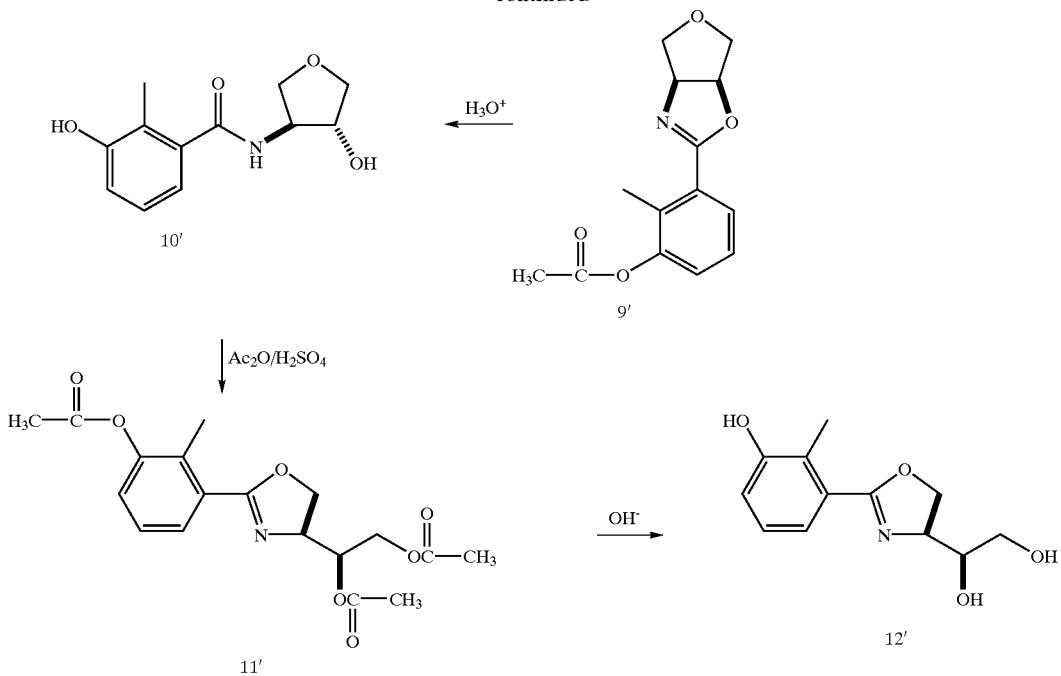

As illustrated in Scheme V, treatment of triol 12' with p-toluenesulfonyl chloride or another substituted or unsubstituted alkyl or aryl sulfonyl chloride in the presence of a base, such as, for example, triethylamine, provides the primary tosylate, Compound 13'. Treatment with this tosylate with a nucleophile, 3S,4aR,8aR-3-N-t-butylcarboxamidodecahydroisoquinoline (PHIQ) in the presence of a base, under conventional conditions, provides Compound 19'. Conversion of Compound 19' into nelfinavir can be accomplished, under conventional conditions, for example, by treatment with thiophenol.

Scheme V

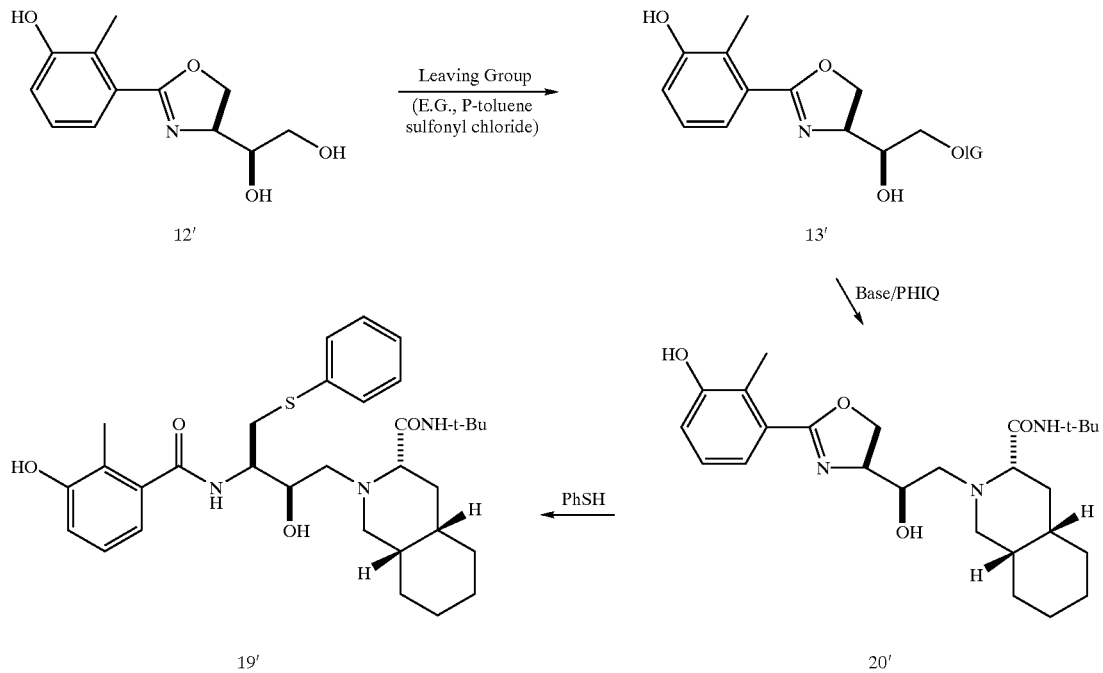

Another embodiment of this invention, illustrated in Scheme VI, provides for the preparation of amino alcohol, 1, from fused epoxy-tetrahydrofuran, 14. Treatment of 1 with (S)-α-methylbenzylamine, or another chiral amine, containing at least 97.5% of a single enantiomer, results in the opening of the epoxide to provide a mixture of diastereomeric Compounds 15' and 16'. This reaction may be conducted using an appropriate solvent such as a mixture of isopropyl amine and water. Crystallization of the diastereomers selectively provides Compound 15'. De-protection of the benzyl moiety of Compound 15' may be conducted using conventional procedures, e.g. hydrogenolysis (hydrogen in the presence of 5% palladium on carbon). The aminoalcohol, 1, is hygroscopic and is preferably isolated as a salt, for example, as the p-toluenesulfonic acid salt, 17.

Scheme VI

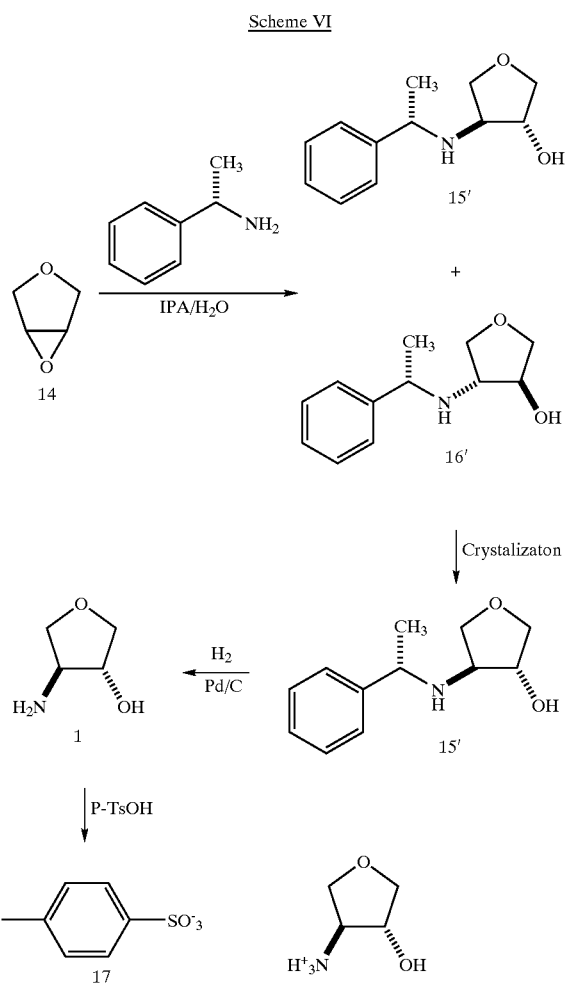

Alternatively, the chiral amino-tetrahydrofuran, 1, may be prepared from the fused epoxy-tetrahydrofuran, 14, using aqueous ammonia, an achiral reagent, to provide a mixture of racemic 1 and 1', which may be resolved using conventional resolution techniques, as illustrated in Scheme VII. For example, the racemic amino-compound may be treated with a chiral acid to form a mixture of diastereomeric salts, which may then be separated by crystallization or chromatography. Neutralization and extractive work-up provides diastereomerically pure amino-tetrahydrofuran, 1, and recovery of the chiral acid.

Scheme VII

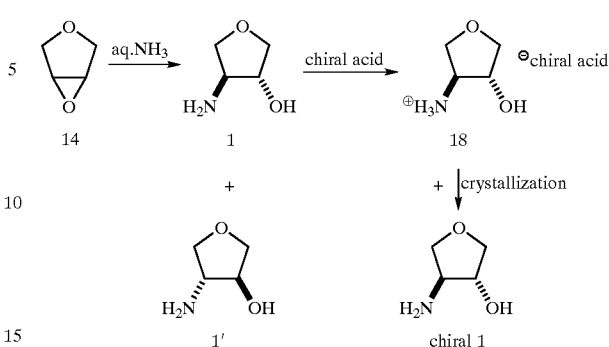

Chiral acids that may be used in the resolution of racemic amino-tetrahydrofuran, 1, include L-tartaric acid, (1R)-(−)-10-camphorsulfonic acid, L-2-pyrrolidone-5-carboxylic acid, (−)-di-O,O'-benzoyl-L-tartaric acid, (−)-mono-(1R)-methyl phthalate, S (+) mandelic acid, L-aspartic acid, (−)-di-O,O'-benzoyl-L-tartaric acid mono(dimethylamide), (−)-2,3:4,6-di-O-isopropylidene-2-keto-L-gulonic acid, L(−)-malic acid, and D(−)-quinic acid.

It is understood that the compounds described herein may exist in different forms, such as stable and metastable crystalline forms and isotropic and amorphous forms, all of which are included within the scope of this invention.

As used herein, the term "PHIQ" refers to the reagent 3S,4aR,8aR-3-N-t-butylcarboxamidodecahydroisoquinoline, "AMBC" refers to the reagent 3-acetoxy-2-methylbenzoyl chloride, "MTBE" refers to the solvent methyl t-butyl ether, "MIBK" refers to the solvent methylisobutyl ketone and "PNB" refers to a p-nitrobenzoyl moiety.

EXAMPLE 1

Synthesis of (3R, 4S) 4-Amino-tetrahydro-furan-3-oltoluene-4-sulfonic Acid Salt, 17

(S)-α-Methylbenzyl amine (304 g, 2.51 mol) and 3,4-epoxytetrahydrofuran 14 (200 g, 2.32 mol) were dissolved in 2-propanol (1 L) and water (1 L). The solution was heated to reflux, with stirring, for 18 hours. The 2-propanol (ca. 1 L) was removed under reduced pressure and water (1 L) was added. The resulting slurry was stirred at room temperature for 16 hours and filtered. The white solids were washed with water (500 mL), then dried in a vacuum oven at room temperature to constant weight to afford crude Compound 15' (170.1 g). The crude material was recrystallized by dissolving the solids in 2-propanol (354 mL) and heptane (1 L) at 60° C. The solution was seeded at 55° C. with pure Compound 15' and allowed to cool to room temperature over 18 hours. The solids were filtered, washed with heptane (200 mL) and dried in a vacuum oven at room temperature to constant weight to give pure Compound 15' (123.2 g, 26%).

A 2 L Parr flask was charged with the pure Compound 15' (120.7 g), 2-propanol (840 mL) and 5% palladium on carbon (12 g). The flask was shaken at 26 psi of hydrogen gas for 44 hours. Additional 5% palladium on carbon (6 g) was added and the mixture was shaken at 26 psi of hydrogen gas for 20 hours. The mixture was filtered through Celite, which was washed with 2-propanol (200 mL). Filtration through Celite and washing was repeated. para-Toluenesulfonic acid (110.8 g) was added to the solution and the solution was concentrated under reduced pressure to 1 L. Methyl-t-butyl ether (MTBE,1.5 L) was added and the resulting solids were filtered, washed with MTBE (250 mL) and dried in a vacuum oven at 40° C. to constant weight to afford pure Compound 17 (138 g, 86%).

EXAMPLE 2

Synthesis of Acetic Acid 3-(4R-hydroxy-tetrahydro-furan-3S-ylcarbamoyl)-2-methyl-phenyl Ester, 2'

The amine salt, 17 (25.0 g, 90.9 mmol) and AMBC (3-acetoxy-2-methylbenzoyl chloride, 20.4 g, 95.9 mmol) were slurried in ethyl acetate (188 mL) at room temperature. With water bath cooling, triethylamine (25.9 mL, 186.1 mmol) was added at a rate sufficient to maintain the temperature below 25° C.. The slurry was stirred at room temperature for 1 hour 45 minutes to give 90.8 mmol of a suspension of tetrahydrofuran-amide, 2'.

EXAMPLE 3

Synthesis of (2R)-1-acetoxy-2-((4S)-2-(3-acetoxy-2-methylphenyl)-4,5-dihydrooxazol-4-yl)-2-methanesulfonyloxyethane, 18'

The reaction product mixture of Example 2 (containing 90.8 mmol of tetrahydrofuran-amide 2') was cooled in an ice/acetone bath and methanesulfonyl chloride (197.6 mL, 227 mmol) was added i n one portion. Triethylamine (19 mL, 136.2 mmol) was added dropwise at a rate sufficient to keep the internal temperature below 1020 C. Acetic anhydride (129 mL, 1362 mmol) was added in one portion and the cooling bath was removed. Sulfuric acid (98%, 38 mL, 681 mmol) was added in three portions at 15 minute intervals. The mixture was stirred at room temperature for 17 hours. A suspension of sodium bicarbonate (305 g, 3632 mmol, 40 equiv.) in 1 liter of water was prepared. This was overlaid with ethyl acetate (250 mL). The reaction mixture from above was added to the sodium bicarbonate slurry dropwise over 2 hours. The layers were separated and the aqueous layer was washed with ethyl acetate (200 mL). The combined organic layers were washed with saturated sodium bicarbonate (200 mL) and brine (200 mL). The organic layer was dried (MgSO$_4$), filtered and evaporated to give 90.8 mmol ofan oil of 18'.

EXAMPLE 4

Synthesis of (3S, 4aS, 8aS)-2-{(2 R)-2-[(4S)-2-(3-Hydroxy-2-methylphenyl)-4,5-dihydrooxazol-4-yl]-2-hydroxyethyl}decahydroisoquinoline-3-carboxylic Acid t-butylamide, 20'

The crude product of Example 3, (2R)-1-acetoxy-2-((4S)-2-(3-acetoxy-2-methylphenyl)-4,5-dihydrooxazol-4-yl)-2methanesulfonyloxyethane, 18'(1.98 kg, 3.30 mol) was suspended in a mixed solvent of methanol (6.50 L) and water (6.50 L), and (3S, 4aS, 8aS)-decahydroisoquinoline-3-carboxylic acid t-butylamide, 642 g, 2.62 mol) and potassium carbonate (1.36 kg, 9.81 mol) were successively added, which was followed by stirring at 50° C. for 5.5 h ours. Water (6.50 L) was added to cool the reaction mixture to room temperature and the resulting crystals were collected by filtration. These crude crystals were again suspended in water (6.50 L), stirred, washed and collected by filtration. The obtained crystals were re-suspended in methyl isobutyl ketone (10.0 L) and the suspension was subjected to azeotropic dehydration. The resulting slurry was cooled to room temperature and crystals were collected by filtration to give 902 g (1.07 mol) of the title compound, as colorless crystals.

Other bases that are suitable for use in this reaction include, sodium carbonate, sodium hydroxide, potassium hydroxide and the like. This reaction may be conducted at a temperature of between −78° C. and 100° C. in a suitable solvent or suitable solvent mixtures including, but not limited to alcoholic solvents (for example, methanol, ethanol, propanol, isopropanol, and the like), water, ethyl acetate, isopropyl acetate, and the like. Preferably, the reaction is conducted as described above.

EXAMPLE 5

Synthesis of (3S, 4aS, 8aS)-2-hydroxy-3-(3-hydroxy-2-methylbenzoyl-amino)-4-phenylthiobutyl]decahydroisoquinoline-3-carboxylic Acid t-butylamide, 19'

(3S, 4aS, 8aS)-2-{(2R)-2-[(4S)-2-(3-Hydroxy-2-methylphenyl)-4,5-dihydrooxazol-4-yl]-2-hydroxyethyl}decahydroisoquinoline-3-carboxylic acid t-butylamide (701 g, 1.53 mol), obtained as in Example 4, was suspended in methyl isobutyl ketone (7.00 L), and thiophenol (314 mL, 3.06 mol) and potassium hydrogencarbonate (76.6 g, 0.765 mol) were added. The mixture was heated to reflux for 12 hours under a nitrogen atmosphere. After the completion of the reaction, toluene (7.00 L) was added, and the precipitated crystals were collected by filtration and washed with toluene. These crude crystals were washed in a mixed solvent of acetone and water (1:1), with heating, to give 695 g (1.22 mol) of the title compound (80% yield) as colorless crystals.

While the invention has been described in terms of various preferred embodiments using specific examples, those skilled in the art will recognize through routine experimentation that various changes and modifications can be made without departing from the spirit and scope of the invention, as defined in the appended claims.

We claim:
1. A method for the preparation of an oxazoline, from a tetrahydrofuran comprising treating the tetrahydrofuran, wherein $R_a$ is —COR(1) and $R_b$ is hydrogen, —COR(3), —SO$_2$R(2) or a suitable hydroxyl protecting group with an oxophilic electrophilic reagent in a manner that is effective to provide the oxazoline, wherein $R_b$ is hydrogen, —COR(3), —SO$_2$R(2) or a suitable hydroxyl protecting group and $R_c$ is hydrogen, —COR(3) or —SO$_2$R(2); wherein R(1), R(2) and R(3) independently represent a substituted or unsubstituted alkyl, aryl, cycloalkyl, heterocycloalkyl or heteroaryl group.

2. The method according to claim 1, comprising treating the tetrahydrofuran with about 1 to about 20 molar equivalents of the oxophilic electrophilic reagent.

3. The method according to claim 1, wherein said oxophilic electrophilic reagent comprises a combination of about 1 to about 20 molar equivalents of a suitable acid and about 1 to about 20 molar equivalents of a suitable acid anhydride, wherein the anhydride and the acid are used in a relative molar ratio of from about 1:5 to about 5:1, respectively.

4. The method according to claim 1, wherein said oxophilic electrophilic reagent comprises a combination of about 2 to about 20 molar equivalents of a suitable acid and about 2 to about 20 molar equivalents of a suitable acid anhydride, wherein the anhydride and the acid are used in a relative molar ratio of from about 1:1 to about 5:1, respectively.

5. The method according to claim 1, wherein said oxophilic electrophilic reagent comprises about 7.5 molar equivalents of a suitable acid and 15 molar equivalents of a suitable acid anhydride.

6. The method according to claim 1 wherein said tetrahydrofuran is treated with an anhydride under acidic conditions to form said oxazoline.

7. A method for the preparation of an oxazoline having the formula:

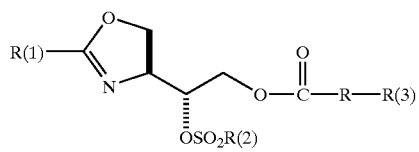

wherein R(1), R(2) and R(3) independently represent substituted or unsubstituted alkyl, aryl, cycloalkyl, heterocycloalkyl or heteroaryl, said method comprising the steps of:

(1) treating an amino-tetrahydrofuran, or a salt thereof, having the formula:

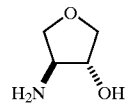

in a manner that is effective to convert said amino-tetrahydrofuran, or a salt thereof, to a tetrahydrofuran-amide, having the formula:

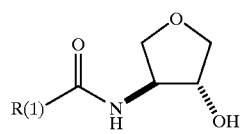

(2) treating the tetrahydrofuran-amide with a substituted or unsubstituted alkyl or aryl sulfonylating reagent to convert said tetrahydrofuran-amide to an tetrahydrofuran amide-sulfonate having the formula:

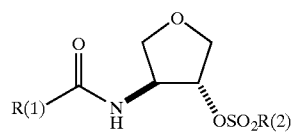

comprising the step-wise treatment of the tetrahydrofuran-amide with at least one molar equivalent amount of the sulfonylating reagent, followed by treatment with a base, wherein the molar equivalent amount of base used in the treatment is less than the molar equivalent amount of the sulfonylating reagent, and (3) treating the tetrahydrofuran amide-sulfonate with an oxophilic electrophilic reagent in a manner that is effective to convert said tetrahydrofuran amide-sulfonate to said oxazoline.

8. A method for the preparation of an oxazoline diol having the formula:

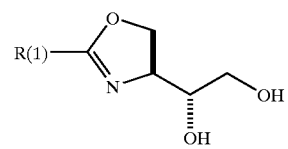

said method comprising the steps of:

(1) treating an amino-tetrahydrofuran, or a salt thereof, having the formula:

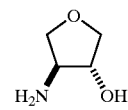

in a manner that is effective to convert the amino-tetrahydrofuran, or a salt thereof, to a tetrahydrofuran-amide having the formula:

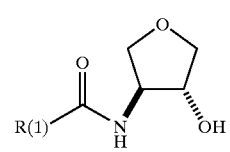

(2) treating the tetrahydrofuran-amide with an oxophilic electrophilic reagent in a manner that is effective to convert said tetrahydrofuran-amide to an oxazoline diester having the formula:

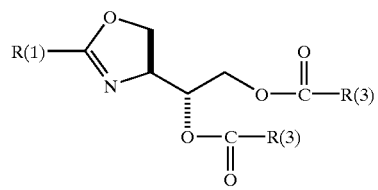

(3) hydrolyzing the oxazoline diester to said oxazoline diol;

wherein R(1) and R(3) independently represent substituted or unsubstituted alkyl, aryl, cycloalkyl, heterocycloalkyl or heteroaryl.

9. A method for the preparation of an oxazoline diol having the formula:

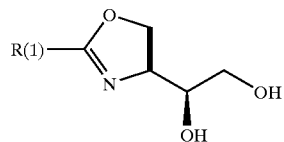

comprising the steps of:

(1) treating an amino-tetrahydrofuran or a salt thereof, having the formula:

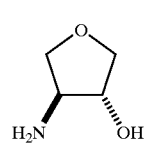

in a manner that is effective to convert the amino-tetrahydrofuran or a salt thereof, to a tetrahydrofuran-amide having the formula:

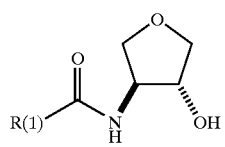

(2) treating the tetrahydrofuran-amide with a substituted or unsubstituted alkyl or aryl sulfonylating reagent, in a manner effective to convert said tetrahydrofuran-amide to a fused tetrahydrofuranyloxazoline having the formula:

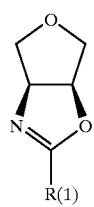

(3) hydrolyzing the fused tetrahydrofuranyloxazoline to a tetrahydrofuran-amide having the formula:

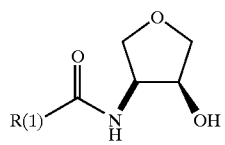

(4) treating the tetrahydrofuran-amide with an oxophilic electrophilic reagent in a manner that is effective to convert said tetrahydrofuran-amide to an oxazoline diester having the formula:

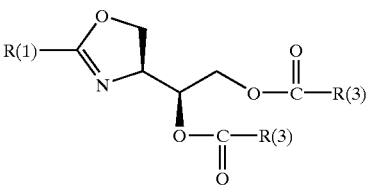

(5) hydrolyzing the oxazoline diester to said oxazoline diol,
wherein R(1) and R(3) independently represent substituted or unsubstituted alkyl, aryl, cycloalkyl, heterocycloalkyl or heteroaryl.

10. A method for the preparation of an oxazoline having the formula:

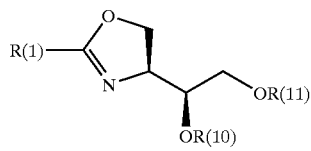

wherein R(1) is substituted or unsubstituted alkyl, aryl, cycloalkyl, heterocycloalkyl or heteroaryl, R(10) is a suitable hydroxyl protecting group and R(11) is H or substituted alkyl sulfonyl, comprising the steps of (1) treating an amino-tetrahydrofuran or a salt thereof, having the formula:

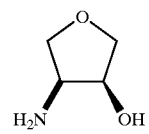

in a manner that is effective to convert the amino-tetrahydrofuran or a salt thereof, to a tetrahydrofuran-hydroxy-amide having the formula:

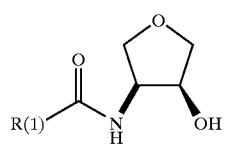

(2) treating the tetrahydrofuran-hydroxy-amide in a manner effective to protect the hydroxyl moiety of the hydroxy-amide to form a protected tetrahydrofuran-amide, having the formula:

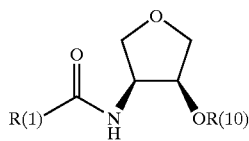

(3) treating the protected tetrahydrofuran-amide with an oxophilic electrophilic reagent in a manner that is effective to convert said tetrahydrofuran-amide to said protected oxazoline;
wherein said oxophilic electrophilic reagent is selected from an oxophilic Lewis acid, an oxophilic protic acid, or triflic anhydride.

11. The method according to any one of claims 1 to 10 wherein R(1) is CF$_3$, a substituted or unsubstituted phenyl, or a C$_1$–C$_6$ alkyl.

12. The method according to any one of claims 1 to 10 wherein R(1) is

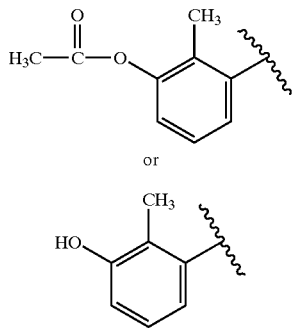

or

13. The method according to any one of claims 7 to 9, comprising treating the tetrahydrofuran with about 1 to about 20 molar equivalents of the oxophilic electrophilic reagent.

14. The method according to any one of claims 7 to 9, wherein said oxophilic electrophilic reagent comprises a combination of about 1 to about 20 molar equivalents of a suitable acid and about 1 to about 20 molar equivalents of a suitable acid anhydride, wherein the anhydride and the acid are used in a relative molar ratio of from about 1:5 to about 5:1, respectively.

15. The method according to any one of claims 7 to 9, wherein said oxophilic electrophilic reagent comprises a combination of about 2 to about 20 molar equivalents of a suitable acid and about 2 to about 20 molar equivalents of a suitable acid anhydride, wherein the anhydride and the acid are used in a relative molar ratio of from about 1:1 to about 5:1, respectively.

16. The method according to any one of claims 7 to 9, wherein said oxophilic electrophilic reagent comprises about 7.5 molar equivalents of a suitable acid and 15 molar equivalents of a suitable acid anhydride.

17. The method according to any one of claims 7 to 9, wherein R(3) is methyl or phenyl.

18. The method according to any one of claims 7 to 9, wherein said tetrahydrofuran-amide is treated with acetic anhydride and sulfuric acidic to form said oxazoline.

19. The method according to claim 11 wherein R(3) is methyl.

20. The method according to any one of claims 7 to 10, wherein the amino-tetrahydrofuran is treated with an compound having the formula R(1)COX, wherein X is chloro or bromo, to form the tetrahydrofuran-amide and R(1) is

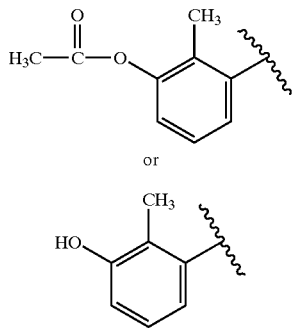

* * * * *